(12) United States Patent
Bhullar et al.

(10) Patent No.: US 7,073,246 B2
(45) Date of Patent: Jul. 11, 2006

(54) METHOD OF MAKING A BIOSENSOR

(75) Inventors: Raghbir S. Bhullar, Indianapolis, IN (US); Eric R. Diebold, Noblesville, IN (US); Brian S. Hill, Avon, IN (US); Nigel A. Surridge, Carmel, IN (US); Douglas P. Walling, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 299 days.

(21) Appl. No.: 10/601,144

(22) Filed: Jun. 20, 2003

(65) Prior Publication Data

US 2004/0194302 A1 Oct. 7, 2004

Related U.S. Application Data

(63) Continuation-in-part of application No. 09/411,940, filed on Oct. 4, 1999, now Pat. No. 6,662,439, and a continuation-in-part of application No. 09/684,257, filed on Oct. 6, 2000, now Pat. No. 6,645,359, and a continuation-in-part of application No. 09/840,843, filed on Apr. 24, 2001, now Pat. No. 6,767,440, and a continuation-in-part of application No. 10/264,891, filed on Oct. 4, 2002.

(51) Int. Cl.
*G01R 3/00* (2006.01)
(52) U.S. Cl. .......................... 29/595; 29/825; 29/846; 29/847; 219/121.69
(58) Field of Classification Search ................ 29/825, 29/846, 847, 595; 219/121.69
See application file for complete search history.

(56) References Cited

U.S. PATENT DOCUMENTS 4,081,653 A * 3/1978 Koo et al. ............. 219/121.68
4,131,484 A 12/1978 Caruso et al. ................. 134/1
4,414,059 A 11/1983 Blum et al. .............. 156/659.1
4,684,437 A 8/1987 Donelon et al. ............ 156/643
4,764,485 A * 8/1988 Loughran et al. ........... 438/690
4,865,873 A 9/1989 Cole, Jr. et al. ........... 427/53.1
4,874,500 A 10/1989 Madou et al. .............. 204/412
4,897,173 A 1/1990 Nankai et al. .............. 204/403
5,018,164 A 5/1991 Brewer et al. .............. 372/109
5,089,103 A 2/1992 Swedberg ................ 204/182.8
5,104,480 A * 4/1992 Wojnarowski et al. ........ 216/65

(Continued)

FOREIGN PATENT DOCUMENTS

EP 0 480 703 A2 4/1992

(Continued)

OTHER PUBLICATIONS

Tender, L. et al., Electrochemical Patterning of Self-Assembled Monolayers onto Microscopic Arrays of Gold Electrodes Fabricated by Laser Ablation, *Langmuir*, 1996, 12, 5515-5518.

(Continued)

*Primary Examiner*—Carl J. Arbes
(74) *Attorney, Agent, or Firm*—Jill L. Woodburn; Justin Sage; Richard Knauer

(57) ABSTRACT

A method of making a biosensor is provided. The biosensor includes an electrically conductive material on a base and electrode patterns formed on the base, the patterns having different feature sizes. The conductive material is partially removed from the base using broad field laser ablation so that less than 90% of the conductive material remains on the base and that the electrode pattern has an edge extending between two points. A standard deviation of the edge from a line extending between two points is less than about 6 μm.

46 Claims, 17 Drawing Sheets

U.S. PATENT DOCUMENTS

| | | | |
|---|---|---|---|
| 5,120,420 A | 6/1992 | Nankai et al. | 204/403 |
| 5,264,103 A | 11/1993 | Yoshioka et al. | 204/403 |
| 5,266,179 A | 11/1993 | Nankai et al. | 204/401 |
| 5,288,636 A | 2/1994 | Pollmann et al. | 435/288 |
| 5,334,279 A | 8/1994 | Gregoire | 156/630 |
| 5,336,388 A | 8/1994 | Leader et al. | 204/406 |
| 5,382,346 A | 1/1995 | Uenoyama et al. | 204/403 |
| 5,390,412 A | 2/1995 | Gregoire | 29/848 |
| 5,391,250 A | 2/1995 | Cheney, II et al. | 156/268 |
| 5,395,504 A | 3/1995 | Saurer et al. | 204/403 |
| 5,413,690 A | 5/1995 | Kost et al. | 204/403 |
| 5,414,224 A | 5/1995 | Adasko et al. | 174/262 |
| 5,426,850 A | 6/1995 | Fukutomi et al. | 29/848 |
| 5,437,999 A | 8/1995 | Diebold et al. | 435/288 |
| 5,451,722 A | 9/1995 | Gregoire | 174/261 |
| 5,465,480 A | 11/1995 | Karl et al. | 29/825 |
| 5,496,453 A | 3/1996 | Uenoyama et al. | 205/777.5 |
| 5,508,171 A | 4/1996 | Walling et al. | 205/777.5 |
| 5,509,410 A | 4/1996 | Hill et al. | 128/637 |
| 5,512,489 A | 4/1996 | Girault et al. | 205/777.5 |
| 5,575,930 A | 11/1996 | Tietje-Girault et al. | 216/65 |
| 5,576,073 A | 11/1996 | Kickelhain | 427/555 |
| 5,589,326 A | 12/1996 | Deng et al. | 435/4 |
| 5,593,739 A | 1/1997 | Kickelhain | 427/555 |
| 5,628,890 A | 5/1997 | Carter et al. | 204/403 |
| 5,635,054 A | 6/1997 | Girault et al. | 205/775 |
| 5,643,472 A * | 7/1997 | Engelsberg et al. | 216/65 |
| 5,682,884 A | 11/1997 | Hill et al. | 128/637 |
| 5,708,247 A | 1/1998 | McAleer et al. | 204/403 |
| 5,739,039 A | 4/1998 | Girault et al. | 436/149 |
| 5,755,953 A | 5/1998 | Henning et al. | 205/778 |
| 5,758,398 A | 6/1998 | Rijnbeek et al. | 29/25.42 |
| 5,759,364 A | 6/1998 | Charlton et al. | 204/403 |
| 5,762,770 A | 6/1998 | Pritchard et al. | 204/403 |
| 5,773,319 A | 6/1998 | Chu et al. | 438/39 |
| 5,798,031 A | 8/1998 | Charlton et al. | 204/403 |
| 5,858,801 A * | 1/1999 | Brizzolara | 436/518 |
| 5,948,289 A | 9/1999 | Noda et al. | 219/121.69 |
| 5,955,179 A | 9/1999 | Kickelhain et al. | 428/210 |
| 5,956,572 A | 9/1999 | Kidoguchi et al. | 438/96 |
| 5,965,001 A | 10/1999 | Chow et al. | 204/600 |
| 6,004,441 A | 12/1999 | Fujiwara et al. | 204/412 |
| 6,103,033 A | 8/2000 | Say et al. | 156/73.1 |
| 6,134,461 A | 10/2000 | Say et al. | 600/345 |
| 6,175,752 B1 | 1/2001 | Say et al. | 600/345 |
| 6,203,952 B1 | 3/2001 | O'Brien et al. | 430/17 |
| 6,258,229 B1 | 7/2001 | Winarta et al. | 205/403 |
| 6,287,451 B1 | 9/2001 | Winarta et al. | 205/777.5 |
| 6,299,757 B1 | 10/2001 | Feldman et al. | 205/775 |
| 6,309,526 B1 | 10/2001 | Fujiwara et al. | 204/403 |
| 6,338,790 B1 | 1/2002 | Feldman et al. | 205/777.5 |
| 6,399,258 B1 | 6/2002 | O'Brien et al. | 430/17 |
| 6,465,594 B1 | 10/2002 | Tamao et al. | 428/207 |
| 6,617,541 B1 * | 9/2003 | Wadman et al. | 219/121.69 |
| 6,662,439 B1 | 12/2003 | Bhullar | 29/825 |
| 6,696,008 B1 | 2/2004 | Brandinger | 264/400 |
| 2001/0006766 A1 | 7/2001 | O'Brien et al. | |
| 2003/0088166 A1 | 5/2003 | Say et al. | |

FOREIGN PATENT DOCUMENTS

| | | |
|---|---|---|
| EP | 0 480 703 B1 | 3/1997 |
| EP | 0 875 754 | 11/1998 |
| EP | 1 152 239 A1 | 11/2000 |
| EP | 1 195 441 A1 | 4/2002 |
| EP | 1 202 060 A1 | 5/2002 |
| EP | 1 203 956 A2 A3 | 5/2002 |
| EP | 1 288 654 A1 | 3/2003 |
| JP | 56100451 | 8/1981 |
| JP | 5-31 5703 | 11/1993 |
| JP | 7-66499 | 3/1995 |
| JP | 7-290751 | 11/1995 |
| JP | 189675 | 4/1997 |
| JP | 9-260697 | 10/1997 |
| JP | 10-52780 | 2/1998 |
| JP | 10-241992 | 9/1998 |
| JP | 10-275959 | 10/1998 |
| JP | 10-303444 | 11/1998 |
| JP | 11297890 | 10/1999 |
| JP | 2000-121594 | 4/2000 |
| WO | WO 91/02391 | 2/1991 |
| WO | WO 91/08474 | 6/1991 |
| WO | WO 95/22881 | 8/1995 |
| WO | WO 98/35225 | 8/1998 |
| WO | WO 98/49773 | 12/1998 |
| WO | WO 98/55856 | 12/1998 |
| WO | WO 99/13101 | 3/1999 |
| WO | WO 99/30152 | 6/1999 |
| WO | WO 99/45387 | 9/1999 |
| WO | WO 00/42472 A1 | 7/2000 |
| WO | WO 00/73778 | 12/2000 |
| WO | WO 00/73785 | 12/2000 |
| WO | WO 01/25775 | 4/2001 |
| WO | WO 01/36953 | 5/2001 |
| WO | WO 01/75438 | 10/2001 |
| WO | WO 01/92884 | 12/2001 |
| WO | WO 02/27074 | 4/2002 |
| WO | WO 02/086483 | 10/2002 |

OTHER PUBLICATIONS

Tahhan, Isam, "Biocompatible Microstructuring of Polymers and Electrodes with an Excimer Laser", MEDICS Workshop 2000 Speakers Abstracts, 2 pp.

Sheppard, Jr. et al. "Electrical Conductivity Measurements Using Microfabricated Interdigitated Electrodes", Anal. Chem., 1993, 65, 1199-1202.

Srinivasan R., et al., "Ultraviolet Laser Ablation of Organic Polymers", Chem. Rev., 1989, 89, 1303-1316.

Zongyi, Q., et al. "Excimer Laser Patterning on Thin Polymer Surfaces for Electrochemical Gas Sensors", Polymer Physics Laboratory, Changchun Institute of Applied Chemistry, Chinese Academy of Sciences, Changchun, Peop. Rep. China., Proceedings of the International Conference on Lasers (1999) 21st (Abstract) 1 pp.

Vaucher et al. "Laser Direct Imaging and Structuring: An Update", http://www.circuitree.com/CDA/ArticleInformation/features/BNP_Features_Item/0,2133,81173,00.html; posted on: Aug. 1, 2002.

Wu, J. et al. "Single-shot Excimer Laser Ablation of Thick Polymer Resists on Metallic Substrates", AMP Journal of Technology vol. 1 Nov., 1991, 69-79.

Srinivasan, R., "Ablation of Polymers and Biological Tissue by Ultraviolet Lasers", Science, vol. 234, Oct. 21, 1986, 559-564.

Colon, W., "Microanalysis: Biosensors at the Point of Care", MST News Jan. 2004, pp. 9-11.

Duley, W.W. "UV Lasers: effects and applications in materials science", Chapter 3 Photochemical and photothermal effects, Cambridge University Press, pp. 78-97.

* cited by examiner

METHOD OF MAKING A BIOSENSOR

CROSS-REFERENCE TO RELATED APPLICATIONS

The present application is a Continuation-in-Part of U.S. application Ser. No. 09/411,940, filed Oct. 4, 1999 now U.S. Pat. No. 6,662,439; a Continuation-in-Part of U.S. application Ser. No. 09/684,257 filed Oct. 6, 2000 now U.S. Pat. No. 6,645,359; a Continuation in Part of U.S. patent application Ser. No. 09/840,843, filed Apr. 24, 2001 now U.S. Pat. No. 6,767,440; and a Continuation in Part of U.S. application Ser. No. 10/264,891, filed Oct. 4, 2002, each of which are hereby incorporated by reference in its entirety.

FIELD OF THE INVENTION

The present invention relates to a method of making a biosensor, more specifically a biosensor having electrode sets formed by laser ablation.

BACKGROUND AND SUMMARY OF THE INVENTION

Electrochemical biosensors are well known and have been used to determine the concentration of various analytes from biological samples, particularly from blood. Examples of such electrochemical biosensors are described in U.S. Pat. Nos. 5,413,690; 5,762,770 and 5,798,031; and 6,129,823 each of which is hereby incorporated by reference.

It is desirable for electrochemical biosensors to be able to analyze analytes using as small a sample as possible, and therefore it is necessary to minimize the size its parts, including the electrodes, as much as possible. As discussed below, screen-printing, laser scribing, and photolithography techniques have been used to form miniaturized electrodes.

Electrodes formed by screen-printing techniques are formed from compositions that are both electrically conductive and which are screen-printable. Furthermore, screen printing is a wet chemical technique that generally allows for the reliable formation of structures and patterns having a gap width or feature size of approximately 75 µm or greater. Such techniques are well known to those of ordinary skill in the art.

Laser scribing is a technique that usually uses a high power excimer laser, such as a krypton-fluoride excimer laser with an illumination wavelength of 248 nm, to etch or scribe individual lines in the conductive surface material and to provide insulating gaps between residual conductive material which forms electrodes and other desired components. This scribing is accomplished by moving the laser beam across the surface to be ablated. The scribing beam generally has a relatively small, focused size and shape, which is smaller than the features desired for the product, and the formation of the product therefore requires rastering techniques. It is therefore appreciated that such a technique can be rather time consuming if a complex electrode pattern is to be formed on the surface. Still further, it is appreciated that the precision of the resulting edge is rather limited. This scribing technique has been used to ablate metals, polymers, and biological material. Such systems are well known to those of ordinary skill in the art, and are described in U.S. Pat. Nos. 5,287,451, 6,004,441, 6,258,229, 6,309,526, WO 00/73785, WO 00/73788, WO 01/36953, WO 01/75438, and EP 1 152 239 each of which is hereby incorporated by reference. It would be desirable to have a new method of forming electrodes which allows precise electrode edges, a variety of feature sizes, and which can be formed in a high speed/throughput fashion without the use of rastering.

According to the present invention a method of making a biosensor electrode pattern is provided. The method comprises the steps of providing an electrically conductive material on a base and forming electrode patterns on the base using broad field laser ablation. In one aspect at least two electrode patterns are formed on the base that have different feature sizes.

According to the present invention a method of making a biosensor is provided. The method comprises the steps of providing an electrically conductive material on a base and partially removing the conductive material from the base using laser ablation so that less than 90% of the conductive material remains on the base and at least one electrode pattern is formed from the conductive material. In one aspect, at least one electrode pattern has an edge extending between two points, a standard deviation of the edge from a line extending between two points being less than about 6 µm along the length of the edge.

According to the present invention a method of making a biosensor is provided. The method comprises the steps of providing an electrically conductive material on a base, forming electrode patterns on the base using broad field laser ablation, wherein at least two electrode patterns have different feature sizes, and extending a cover over the base. In one aspect, the cover and base cooperate to define a sample-receiving chamber and at least a portion of the electrode patterns are positioned in the sample-receiving chamber.

According to the present invention a method of making a biosensor electrode set is provided. The method comprises providing a laser system having a lens and a mask, and ablating through a portion of a first metallic layer with a laser, to form an electrode pattern, the pattern of ablation being controlled by the lens and the mask. In one aspect, the metallic layer is on an insulating base.

According to another aspect of the present invention, a method of making a biosensor strip is provided. The method comprises providing a laser system having at least a laser source and a mask, and forming an electrode set by ablating through a portion of a metallic layer with a laser, a pattern of ablation being controlled by the mask, wherein said metallic layer is on an insulating base.

Still further, according to the present invention a method of making a biosensor is provided. The method comprises providing an electrically conductive material on a base and forming a pre-determined electrode pattern on the base using laser ablation through a mask, the mask having a mask field with at least one opaque region and at least one window formed to allow a laser beam to pass through the mask and to impact predetermined areas of the electrically conductive material.

According to the present invention a method of making a biosensor electrode set is provided. The method comprises providing a laser system having a lens and a mask, ablating through a portion of a metallic layer with a laser, to form an electrode pattern, the pattern of ablation being controlled by the lens and the mask, wherein said first metallic layer is on an insulating substrate.

According to the present invention a method of making an electrode set ribbon is provided. The method comprises providing a laser system having a lens and a mask and ablating through a portion of a metallic layer with a laser, to form a plurality of electrode patterns. The pattern of ablation is controlled by the lens and the mask, the metallic layer is on an insulating substrate, and the electrode set ribbon comprises a plurality of electrode sets.

Still further according to the present invention a method of making a sensor strip is provided. The method comprises providing a laser system having a lens and a mask, forming an electrode set by ablating through a portion of a first metallic layer with a laser, and cutting said substrate, to form a strip. A pattern of ablation is controlled by the lens and the mask and the first metallic layer is on an insulating substrate.

The following definitions are used throughout the specification and claims:

As used herein, the phrase "electrically conductive material" refers to a layer made of a material that is a conductor of electricity, non-limiting examples of which include a pure metal or alloys.

As used herein, the phrase "electrically insulative material" refers to a material that is a nonconductor of electricity.

As used herein, the term "electrode" means a conductor that collects or emits electric charge and controls the movement of electrons. An electrode may include one or more elements attached to a common electrical trace and/or contact pad.

As used herein, the term "electrical component" means a constituent part of the biosensor that has electrical functionality.

As used herein, the phrase "electrode system" refers to an electrical component including at least one electrode, electrical traces and contacts that connect the element with a measuring instrument.

As used herein, the phrase "electrode set" is a grouping of at least two electrodes that cooperate with one another to measure the biosensor response.

As used herein, the term "pattern" means a design of one or more intentionally formed gaps, a non-limiting example of which is a single linear gap having a constant width. Not included in the term "pattern" are natural, unintentional defects.

As used herein, the phrase "insulative pattern" means a design of one or more intentionally formed gaps positioned within or between electrically insulative material(s). It is appreciated that electrically conductive material may form the one or more gaps.

As used herein, the phrase "conductive pattern" means a design of one or more intentionally formed gaps positioned within or between electrically conductive material(s). It is appreciated that exposed electrically insulative material may form the one or more gaps.

As used herein, the phrase "microelectrode array" means a group of microelectrodes having a predominantly spherical difusional characteristic.

As used herein, the phrase "macroelectrode array" means a group of macroelectrodes having a predominantly radial diffusional characteristic.

As used herein, the phrase "electrode pattern" means the relative configuration of the intentionally formed gaps situated between the elements of electrodes in an electrode set. Non-limiting examples of "electrode patterns" include any configuration of microelectrode arrays and macroelectrode arrays that are used to measure biosensor response.

As used herein, the phrase "feature size" is the smallest dimension of gaps or spaces found in a pattern. For example, in an insulative pattern, the feature size is the smallest dimension of electrically conductive gaps found within or between the electrically insulative material(s). When, however, the pattern is a conductive pattern, the feature size is the smallest dimension of electrically insulative gaps found within or between the electrically conductive material(s). Therefore, in a conductive pattern the feature size represents the shortest distance between the corresponding edges of adjacent elements.

As used herein, the term "interlaced" means an electrode pattern wherein the elements of the electrodes are interwoven relative to one another. In a particular embodiment, interlaced electrode patterns include electrodes having elements, which are interdigitated with one another. In the simplest form, interlaced elements include a first electrode having a pair of elements and a second electrode having a single element received within the pair of elements of the first electrode.

As used herein, the term "ablating" means the removing of material. The term "ablating" is not intended to encompass and is distinguished from loosening, weakening or partially removing the material.

As used herein, the phrase "broad field laser ablation" means the removal of material from a substrate using a laser having a laser beam with a dimension that is greater than the feature size of the formed pattern. Broad field ablation includes the use of a mask, pattern or other device intermediate a laser source and a substrate, which defines a pattern in which portions of the laser beam impinge on the substrate to create variable and multiple patterns on the substrate. Broad field laser ablation simultaneously creates the pattern over a significant area of the substrate. The use of broad field laser ablation avoids the need for rastering or other similar techniques that scribe or otherwise define the pattern by continuous movement of a relatively focused laser beam relative to the substrate. A non-limiting example of a process for broad field laser ablation is described below with reference to biosensor 210.

As used herein, the term "line" means a geometric figure formed by a point moving in a first direction along a pre-determined linear or curved path and in a reverse direction along the same path. In the present context, an electrode pattern includes various elements having edges that are defined by lines forming the perimeters of the conductive material. Such lines demarcating the edges have desired shapes, and it is a feature of the present invention that the smoothness of these edges is very high compared to the desired shape.

As used herein, the term "point" means a dimensionless geometric object having no properties except location.

As used herein, the term "smooth" means an edge of a surface deviating from a line extending between two points not more than about 6 μm. Further, for patterns having a feature size of about 5 μm or less, "smooth" means an edge of a surface deviating from a line extending between two points less than one half the feature size of the conductive pattern. For example, such lines demarcate the edges that have desired shapes, and the smoothness of these edges is very high compared to the desired shape.

As used herein, the phrase "biological fluid" includes any bodily fluid in which the analyte can be measured, for example, interstitial fluid, dermal fluid, sweat, tears, urine, amniotic fluid, spinal fluid and blood.

As used herein, the term "blood" includes whole blood and its cell-free components, namely plasma and serum.

As used herein, the term "working electrode" is an electrode at which analyte, or product, is electrooxidized or electroreduced with or without the agency of a redox mediator.

As used herein, the term "counter electrode" refers to an electrode that is paired with the working electrode and through which passes an electrochemical current equal in magnitude and opposite in sign to the current passed through the working electrode. The term "counter electrode" is meant to include counter electrodes, which also function as reference electrodes (i.e., a counter/reference or auxiliary electrode).

As used herein, the term "electrochemical biosensor" means a device configured to detect the presence and/or measure the concentration of an analyte by way of electrochemical oxidation and reduction reactions within the biosensor. These reactions are transduced to an electrical signal that can be correlated to an amount or concentration of the analyte.

Additional features of the invention will become apparent to those skilled in the art upon consideration of the following detailed description of the preferred embodiment exemplifying the best mode known for carrying out the invention. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
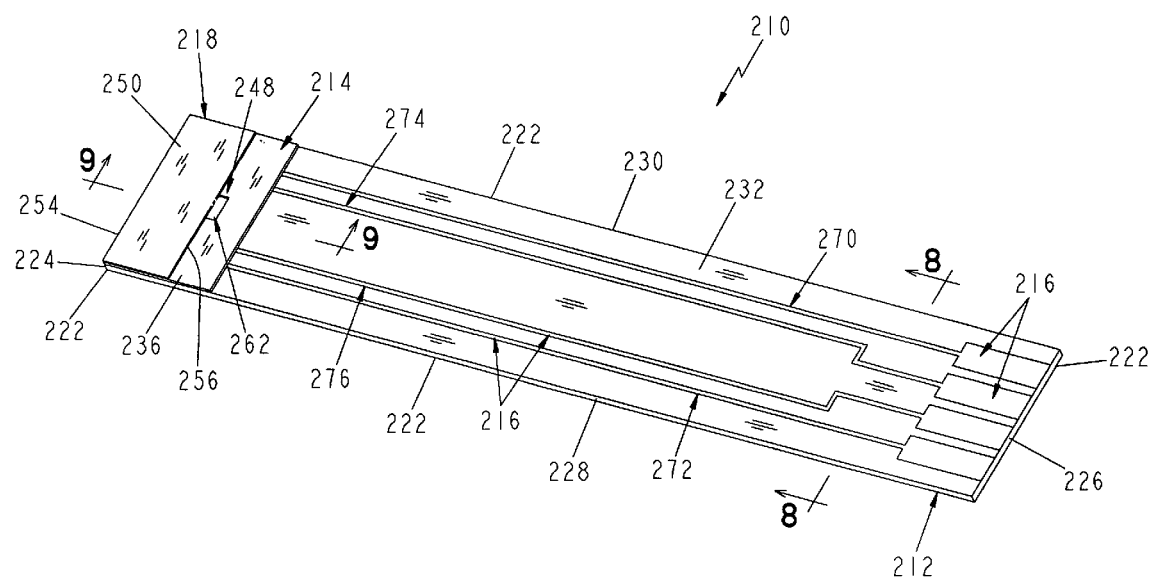
FIG. 1 illustrates a perspective view of a biosensor of the present invention.

For the purposes of promoting an understanding of the principles of the invention, reference will now be made to the embodiments illustrated in the drawings, and specific language will be used to describe the embodiments. It will nevertheless be understood that no limitation of the scope of the invention is intended. Alterations and modifications in the illustrated devices, and further applications of the principles of the invention as illustrated therein, as would normally occur to one skilled in the art to which the invention relates are contemplated, are desired to be protected.

A biosensor in accordance with the present invention provides a surface with electrode patterns formed thereon, the electrode patterns preferably having a smooth edge quality. It is a particular aspect of the present invention that precise quality is obtained for the edges of the electrical components located on the biosensor. Having a smooth or high edge quality of the elements can contribute to greater precision, accuracy, and reproducibility of test results. Further, a smooth or high edge quality also allows for a great number of electrode arrays to be formed on a defined surface area of the biosensor. By increasing the edge quality of the elements, it is possible to increase the number of electrode elements and thus increase the achievable functionality in the defined surface area. These functions may include, for example: multiple measurement electrode pairs for simultaneous measurement of the same or different analytes, including by alternative means; electrodes used to provide correction factors for the basic measurement electrodes; electrodes for detecting dose application or sample sufficiency; multiple electrode traces to monitor electrode functioning or to provide detection or correction of defective traces; and multiple contact pads for coupling to the foregoing functionalities, or for providing additional features such as identification, calibration, or other information pertaining to the biosensor. Further, the selected functionalities for a given biosensor can be provided in a smaller space when the high edge quality allows closer placement of the electrical components. It is a feature of the present invention to enable all of this, and more, in a manner that is relatively fast, reliable and cost effective.

Specifically, a biosensor of the present invention has electrical components with edges that are smooth and are precisely located. The precise locating of the smooth edge is important, particularly relative to a corresponding edge of another electrical component, and especially with respect to a paired element. The importance and the degree of quality of a component's edge quality and placement will vary with the nature of the component.

For macroelectrodes, it is noted that the edge smoothness and placement are important for the quality of the electrochemical results obtained by use of the macroelectrodes. One factor in the accuracy of such a test is the reproducibility of the area of each macroelectrode. The provision of precise edge smoothness and placement will yield an area that is highly accurate. Another factor in the use of macroelectrodes is the placement of one of the electrodes relative to the other, e.g., the position of the counter element(s) in relationship to the position of the working element(s). Moreover, since biosensors are generally operated based on calibration methods that rely on the reproducibility of the sizes and locations of the measuring electrodes, the ability to consistently produce lots of such tests trips can enhance the results achieved with the tests.

Similarly, the edge smoothness and placement contribute to the results obtained from microelectrodes. For microelectrodes, the issues can be magnified because of the number and relatively close placement of the numerous microelements. Poor edge quality can greatly change the operating characteristics of microelectrodes, and the present invention helps to overcome this potential problem. Moreover, an advantage of placing microelements in close proximity is the rapid establishment of steady-state operation. The provision of high edge quality and precise edge placement enables closer placement of the elements, and therefore faster achievement of steady-state operation. In addition, such closer placement allows for a greater number of microelements to be placed in a given space.

The foregoing discussion also applies to various other electrical components on the biosensor. Other types of electrodes may be employed on a biosensor, for example to detect dose application or sample sufficiency, or to provide correction factors for hematocrit, temperature, etc. In addition to enhancing the results obtained from such additional electrode systems, the present invention allows for the inclusion of such additional functionalities in a small space. This allows the inclusion of such features while maintaining the overall sample-receiving chamber at a small volume.

Still further, the edge smoothness and placement accuracy contribute to the ability to place an increased number of traces in a limited space on a biosensor. Thus, the present invention allows for multiple functionalities on a single biosensor requiring the use of a corresponding number, or more, of electrical traces.

The contact pads are also enhanced in view of the high quality of the edge smoothness and placement. The increased number of functionalities on a single biosensor requires a related increase in the number of contact pads, which must fit on an already crowded area of the typical biosensor. The ability to pack more contact pads and associated electrical components onto the biosensor can greatly increase the utility of the biosensor.

Figure 22:
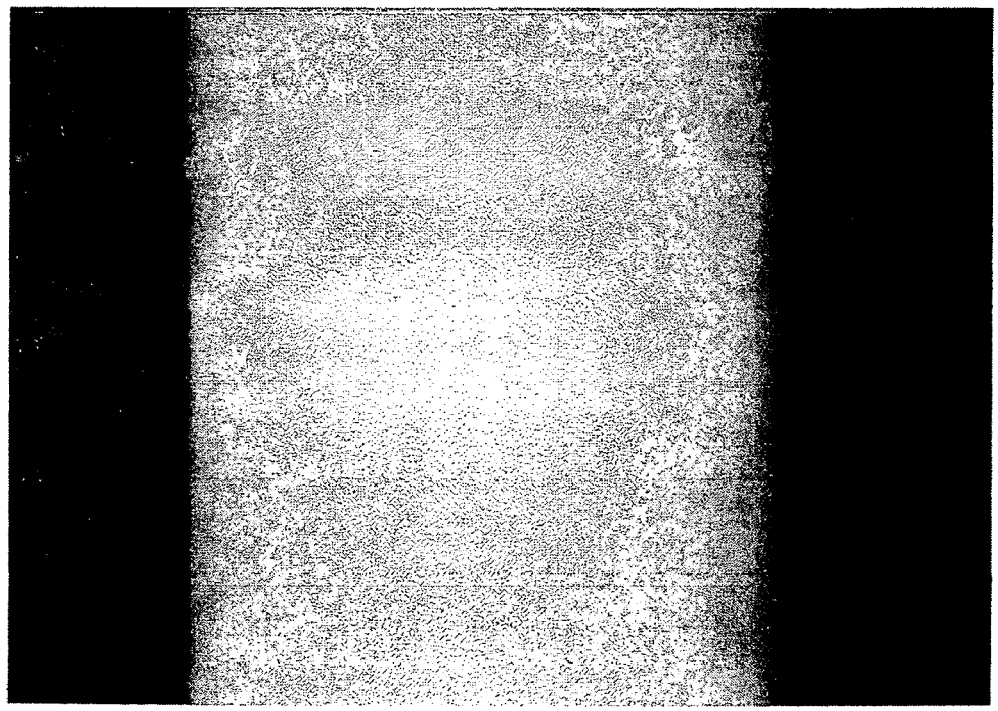
FIG. 22 is a microscopic view of a portion of an electrical component having a relatively "smooth" edge.

In a first aspect, the present invention provides a high quality edge for the various electrical components on a biosensor. The quality of the edge relates to the smoothness or uniformity of the edge relative to a theoretical profile of the edge. A non-limiting example of such a "smooth" edge formed in accordance with teachings of the present disclosure is shown in FIG. 22.

In one respect, the smoothness relates simply to the deviation of the edge surface relative to the theoretical line defining the desired shape of the edge. It will be appreciated that any electrical component on a biosensor has an intended location and shape that will not be exactly duplicated by the physical embodiment. The extent to which the actual edge of the component varies from the theoretical one is a measure of the smoothness of the edge. As previously discussed, a smooth edge is defined herein as an edge for which the standard deviation for the distances by which the actual edge points vary from the theoretical edge configuration do not vary by more than a given amount. This variation is referred to herein as the "smoothness standard deviation". In one aspect, the smoothness standard deviation is less than about 6 μm, preferably less than about 2 μm, and more preferably less than about 1.0 μm.

As relates to the various electrical components, the extent to which a given portion of the component is "smooth" may vary. Referring in particular to the measuring electrodes, it will be appreciated that certain edges of the elements are more critical than others. For example, certain edges of the counter and working electrodes are adjacent one another, while others are not. Also, certain edges are located within the sample-receiving chamber, and others are not. In a first aspect, the present invention relates to providing smooth edges for all of the edges of the measuring electrodes. In another aspect, the invention provides smooth edges particularly for the edges of the measuring electrodes located within the sample-receiving chamber, and more particularly for the edges of the measuring elements that are adjacent to one another. "Adjacent edges" in this context refers to the fact that an edge of a counter element is closest to, i.e., adjacent to, an edge of an element of a working electrode with which the counter electrode is paired. Preferably, the edge of a measuring electrode that comprises an adjacent edge has a smoothness standard deviation of less than about 2 μm, more preferably less than about 1 μm.

As indicated previously, the present invention relates in one aspect to providing macroelectrodes having a closely determined area. The desired accuracy of the provided area can vary based on the absolute size of the macroelectrode. As contemplated by the present invention, it is an aspect that the smoothness of the edge of a macroelectrode has a standard deviation of less than about 4 μm to about 6 μm along the entire length of that edge, more preferably less than about 2 μm, and most preferably less than about 1 μm. Non-limiting examples of a suitable length of the edge are about 50 μm to about 1.5 mm, preferably about 250 μm to about 1 mm.

The spacing of macroelectrodes also can benefit from the present invention. For example, for macroelectrodes that are spaced apart by 250 μm, the adjacent edges preferably have a smoothness represented by a standard deviation (from theoretical) of less than about 4 μm; for elements spaced apart by 100 μm, the standard deviation is preferably less than about 2 μm. In this regard, the smoothness standard deviation for macroelectrodes is preferably less than about 2% of the gap between adjacent macroelectrodes, more preferably less than about 1% of the gap.

For microelectrodes, the desired smoothness can differ. For example, for microelements that are spaced apart by 50 μm, the adjacent edges have a smoothness represented by a standard deviation (from theoretical) of less than about 6 μm, preferably less than about 2 μm, and most preferably less than about 1 μm. If the microelements are spaced apart by about 10 μm, then the smoothness standard deviation is preferably less than about 1 μm, more preferably less than about 0.5 μm. Still further, if the microelements are spaced apart by less than 1 μm, then the smoothness standard deviation is preferably less than one half the feature size of the microelement pattern. In general, the smoothness standard deviation for microelectrodes is preferably less than about 5% of the gap between adjacent microelements or feature size, more preferably less than about 2% of the gap or feature size.

It is also an aspect of the present invention that the other electrical components can be provided with smooth edges to facilitate close placement of such components. Such other components preferably have a smoothness standard deviation that is less than about 6 µm, and more preferably less than about 2 µm. For spacings less than 1 µm, then the smoothness standard deviation is preferably less than one half the gap between the adjacent electrical components.

The present invention also provides for the accurate placement of the electrical components relative to one another and to the overall biosensor. The relative placement of components is achieved, at least in part, by the use of broad field laser ablation that is performed through a mask or other device that has a precise pattern for the electrical components. The relative placement of the components therefore does not depend on the controlled movement of a rastering laser or of the substrate relative to the rastering laser. Moreover, this accurate positioning of adjacent edges is further enhanced by the close tolerances for the smoothness of the edges.

Therefore, in a further aspect the invention provides electrical components that have gaps or features that are precisely controlled. More specifically, the electrical components will have designed, theoretical configurations for the gaps between adjacent edges, whereas the physical embodiments will have variations and irregularities. The present invention provides gaps between adjacent edges that are highly uniform. Specifically, the present invention provides a "uniform gap", which is defined as a gap for which the "gap standard deviation" for the widths or spacings of the actual edge points, compared to the theoretical spacings, do not vary by more than a given amount. In one aspect, for example, the gap standard deviation is less than about 6 µm along the entire length of the gap. Preferably the gap standard deviation is less than about 2 µm, more preferably less than about 1 µm.

Related to this concept, the accurate gap dimensions for adjacent edges are also obtained by the minimal deviations of the respective edges from the theoretical edges. As previously described, the edge quality is preferably represented by a smoothness standard deviation that is less than about 6 µm. In a related aspect then, the gap formed between two adjacent edges has a gap uniformity in which the standard deviation of the gap width is less than about 6 µm, more preferably less than about 2 µm. Various aspects of the invention are presented in FIGS. 1–20 and 22, which are not drawn to scale and wherein like components in the several views are numbered alike.

It is appreciated that the biosensor of the present invention is suitable for use in a system for assessing an analyte in a sample fluid. In addition to the biosensor, the system includes a meter (not shown) and provides methods for evaluating the sample fluid for the target analyte. The evaluation may range from detecting the presence of the analyte to determining the concentration of the analyte. The analyte and the sample fluid may be any for which the test system is appropriate. For purposes of explanation only, a preferred embodiment is described in which the analyte is glucose and the sample fluid is blood or interstitial fluid. However, the present invention clearly is not so limited in scope.

Non-limiting examples of meters suitable for use with the biosensor of the present invention for determination of the analyte in the sample fluid are disclosed in U.S. Pat. Nos. 4,963,814; 4,999,632; 4,999,582; 5,243,516; 5,352,351; 5,366,609; 5,405,511; and 5,438,271, the disclosures of each being incorporated herein by reference. The suitable meter (not shown) will include a connection with electrodes of the biosensor, and circuitry to evaluate an electrochemical signal corresponding to the concentration of the analyte. The meter may also include electrical components that determine whether the sample fluid has been received by the biosensor and whether the amount of sample fluid is sufficient for testing. The meter typically will store and display the results of the analysis, or may alternatively provide the data to a separate device.

The biosensor of the present invention forming part of the system can provide either a qualitative or quantitative indication for the analyte. In one embodiment, the biosensor cooperates with the meter to indicate simply the presence of the analyte in the sample fluid. The biosensor and meter may also provide a reading of the quantity or concentration of the analyte in the sample fluid. In a preferred embodiment, it is a feature of the present invention that a highly accurate and precise reading of the analyte concentration is obtained.

The biosensor is useful for the determination of a wide variety of analytes. The biosensor, for example, is readily adapted for use with any suitable chemistry that can be used to assess the presence of the analyte. Most preferably, the biosensor configured and used for the testing of an analyte in a biological fluid. Commensurate modifications to the system will be apparent to those skilled in the art. For purposes of explanation, and in a particularly preferred embodiment, the system is described with respect to the detection of glucose in a biological fluid.

The biosensor is also useful with a wide variety of sample fluids, and is preferably used for the detection of analytes in a biological fluid. In addition, the biosensor is useful in connection with reference fluids that are used in conventional fashion to verify the integrity of the system for testing.

In a preferred embodiment, the biosensor is employed for the testing of glucose. The sample fluid in this instance may specifically include, for example, fresh capillary blood obtained from the finger tip or approved alternate sites (e.g., forearm, palm, upper arm, calf and thigh), fresh venous blood, and control solutions supplied with or for the system. The fluid may be acquired and delivered to the biosensor in any fashion. For example, a blood sample may be obtained in conventional fashion by incising the skin, such as with a lancet, and then contacting the biosensor with fluid that appears at the skin surface. It is an aspect of the present invention that the biosensor is useful with very small fluid samples. It is therefore a desirable feature that only a slight incising of the skin is necessary to produce the volume of fluid required for the test, and the pain and other concerns with such method can be minimized or eliminated.

FIGS. 1–10 illustrate an aspect of the invention, which is the forming of an electrochemical biosensor 210. Biosensor 210 has two electrode patterns having different feature sizes on a common planar surface and thus permits the accurate measurement of an analyte in a fluid.

Figure 2:
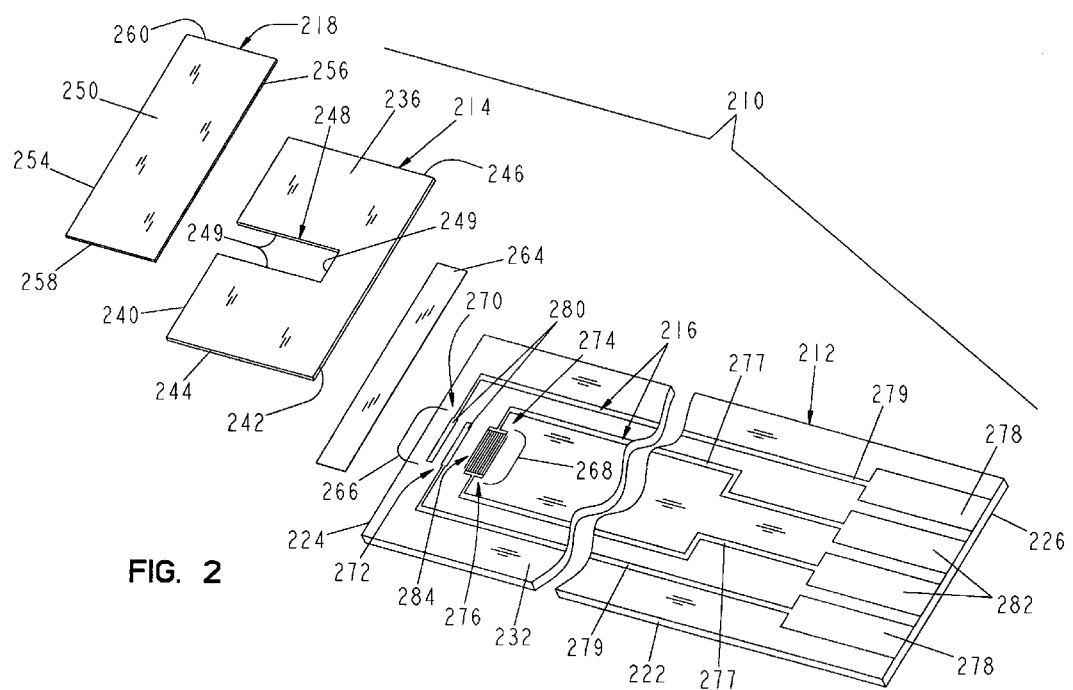
FIG. 2 illustrates an exploded assembly view of the biosensor of FIG. 1.
Figure 9:
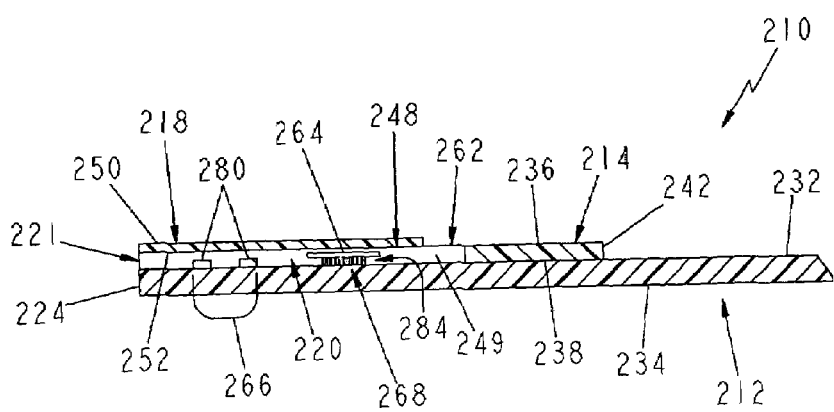
FIG. 9 illustrates a cross-section taken along lines 9—9 of FIG. 1.

As shown in FIG. 1, biosensor 210 comprises a base 212, conductive material 216 positioned on the base 212, a spacer 214, and a cover 218. The cover 218 and spacer 214 cooperate with the base 212 to define a sample-receiving chamber 220 (FIG. 9) having a sample inlet opening 221 for the sample fluid, and a reagent 264 for producing an electrochemical signal in the presence of a test analyte. The biosensor 210 is formed as a test strip, particularly one having a laminar construction providing an edge or surface opening to the sample-receiving chamber 220. The reagent 264, as shown in FIGS. 2 and 9, is exposed by the sample-receiving chamber 220 to provide the electrochemical signal to a working electrode also positioned within the chamber 220. In appropriate circumstances, such as for glucose detection, the reagent may contain an enzyme and optionally a mediator.

Figure 8:
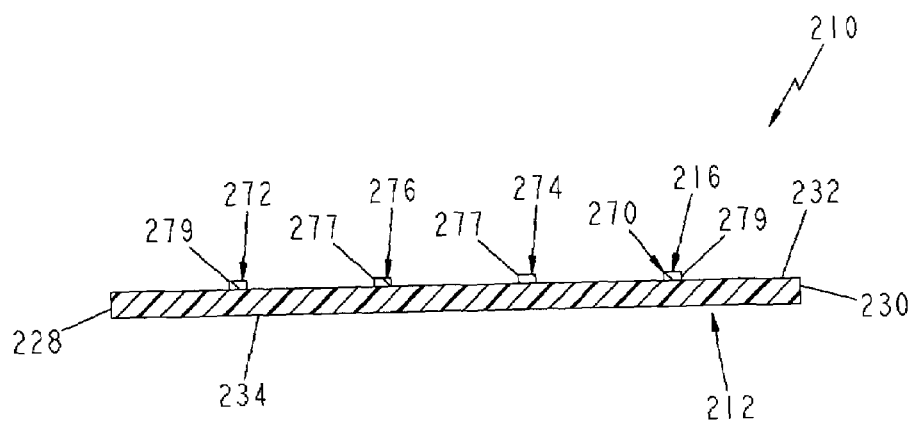
FIG. 8 illustrates a cross-section taken along lines 8—8 of FIG. 1.

The base 212 of biosensor 210 includes edges 222 that define opposite ends 224, 226 and sides 228, 230 extending between the ends 224, 226. Base 212 also has a top surface 232 supporting the conductive material 216 and an opposite bottom surface 234 (FIGS. 8 and 9). Illustratively, base 212 has a length of 40 mm and a width of 10 mm. It is appreciated, however that these values are merely illustrative and that the dimensions of the base 212 may vary in accordance with the present disclosure.

The base 212 is a substrate that is formed from an insulating material, so that it will not provide an electrical connection between electrodes formed from the conductive material 216. Non-limiting examples of suitable insulating materials include glass, ceramics and polymers. Preferably, the base is a flexible polymer and has a strong absorbance in the UV. Non-limiting examples of suitable materials include polyethylene terephtalate (PET), polyethylene naphthalate (PEN), and polyimide films. The suitable films are commercially available as MELINEX®, KALADEX® and KAPTON®, respectively from E.I. duPont de Nemours, Wilmington, Del., USA ("duPont") and UPILEX®, a polyimide film from UBE Industries Ltd, Japan. Preferred materials are selected from 10 mil thick MELINEX® 329 or KAPTON®, which are coated with 50±4 nm gold within-lot C.V. of <5% by: Techni-Met Advanced Depositions, Inc., Windsor, Conn., USA. It is appreciated that the base 212 may be either purchased pre-coated with conductive material 216 or may be coated by sputtering or vapor deposition, in accordance with this disclosure. It is further appreciated that the thickness of the conductive material can vary in accordance with this disclosure.

Spacer 214 is illustratively positioned on the top surface 232 of the base 212 adjacent to end 224. Spacer 214 has an upper surface 236 and a lower surface 238 (FIG. 9) facing the base 212. Referring now to FIG. 2, the spacer 214 has edges 240, 242, 244, 246. Illustratively, spacer 214 has a length of about 6 mm, a width of about 10 mm and a height of about 4 mil. It is appreciated, however that these values are merely illustrative and that the biosensor may be formed without a spacer and that the dimensions of the spacer 214 may vary in accordance with the present disclosure.

Spacer 214 is formed from an insulating material, so that it will not provide an electrical connection between electrodes formed from the conductive material 216. Non-limiting examples of suitable insulating materials include glass, ceramics, polymers, photoimageable coverlay materials, and photoresists—non-limiting examples of which are disclosed in U.S. patent application Ser. No. Ser. No. 10/264,891, filed Oct. 4, 2002, the disclosure of which is incorporated herein by reference. Illustratively, spacer 214 is formed of 4 mil MELINEX® polyester film, which is preferred for use with whole blood samples. It is appreciated, however, that when the sample is plasma or serum, 1–2 mil film may be preferred for use in accordance with this disclosure. It is appreciated, however that these values are merely illustrative and that the composition and dimension of the spacer 214 may vary in accordance with the desired height of the sample-receiving chamber.

A slit 248 is formed in the spacer 214 and extends from the edge 240 toward the edge 242. The slit 248 defines at least the length and width of the sample-receiving chamber 220 and is defined by edges 249. Illustratively, the slit 248 has a length of 5 mm, a width of 1 mm, and a height of 0.1 mm, but may have a variety of lengths and widths in accordance with the present disclosure. It is further appreciated that the edges 249 of the slit may also be curved or angular in accordance with this disclosure.

As shown in FIG. 1, the cover 218 is positioned on the upper surface 236 of spacer 214. Cover 218 has a first surface 250 and a second surface 252 (FIG. 9) facing the base 212. Further, the cover 218 has edges 254, 256, 258, 260. As shown in FIG. 1, the cover 218 has a length that is less than the length of the slit 248. Illustratively, cover 218 has a length of about 4 mm, a width of about 10 mm and a height of about 0.1 mm. It is appreciated, however that these values are merely illustrative and that the biosensor may be formed without a cover and that the dimensions of the cover 218 may vary in accordance with the present disclosure.

The cover 218 is illustratively formed of a clear material having a hydrophilic adhesive layer in proximity to the spacer. Non-limiting examples of materials suitable for cover 218 include polyethylene, polypropylene, polyvinylchloride, polyimide, glass, or polyester. A preferred material for cover 218 is 100 μm polyester. A preferred adhesive is ARCare 8586 having a MA-55 hydrophilic coating, commercially available from Adhesives Research Inc., Glen Rock, Pa. Further, it is appreciated that the cover may have markings in accordance with this disclosure.

The slit 248 in the spacer 214, together with the cover 218, and the base 212, form the sample-receiving chamber 220 (FIG. 9), which acts to expose reagent 264 to a fluid to be tested from a user of biosensor 210. This sample-receiving chamber 220 can act as a capillary channel, drawing the fluid to be tested from the opening 221 onto a sensing region of the conductive material 216 and toward a vent 262. It is appreciated that the biosensor may be formed without a spacer in accordance with this disclosure and that in addition to or instead of the spacer and the cover, a variety of dielectric materials may cover the base 212 exposing only selected portions of the conductive material in accordance with this disclosure. Moreover, it is appreciated that when present, the dimensions of the channel 220 may vary in accordance with this disclosure.

FIG. 2 illustrates the conductive material 216 defining electrode systems comprising a first electrode set 266 and a second electrode set 268, and corresponding traces 279, 277 and contact pads 278, 282, respectively. The conductive material 216 may contain pure metals or alloys, or other materials, which are metallic conductors. Preferably, the conductive material is transparent at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. Preferably, the conductive material includes noble metals or alloys or their oxides. Most preferably, the conductive material includes gold, palladium, aluminum, titanium, platinum, ITO and chromium. The conductive material ranges in thickness from about 10 nm to 80 nm, more preferably, 30 nm to 70 nm. FIGS. 1–3, 6, and 8–9 illustrate the biosensor 210 with a 50 nm gold film. It is appreciated that the thickness of the conductive material depends upon the transmissive property of the material and other factors relating to use of the biosensor.

Illustratively, the conductive material 216 is ablated into two electrode systems that comprise sets 266, 268. In forming these systems, the conductive material 216 is removed from at least about 5% of the surface area of the base 212, more preferably at least about 50% of the surface area of the base 212, and most preferably at least about 90% of the surface area of the base 212. As shown in FIG. 2, the only conductive material 216 remaining on the base 212 forms at least a portion of an electrode system.

While not illustrated, it is appreciated that the resulting patterned conductive material can be coated or plated with additional metal layers. For example, the conductive material may be copper, which is then ablated with a laser, into an electrode pattern; subsequently, the copper may be plated with a titanium/tungsten layer, and then a gold layer, to form the desired electrodes. Preferably, a single layer of conductive material is used, which lies on the base 212. Although not generally necessary, it is possible to enhance adhesion of the conductive material to the base, as is well known in the art, by using seed or ancillary layers such as chromium nickel or titanium. In preferred embodiments, biosensor 210 has a single layer of gold, palladium, platinum or ITO.

As shown in FIGS. 2 and 9, the biosensor 210 includes an electrode system comprising at least a working electrode and a counter electrode within the sample-receiving chamber 220. The sample-receiving chamber 220 is configured such that sample fluid entering the chamber is placed in electrolytic contact with both the working electrode and the counter electrode. This allows electrical current to flow between the electrodes to effect the electrooxidation or electroreduction of the analyte or its products.

Figure 3:
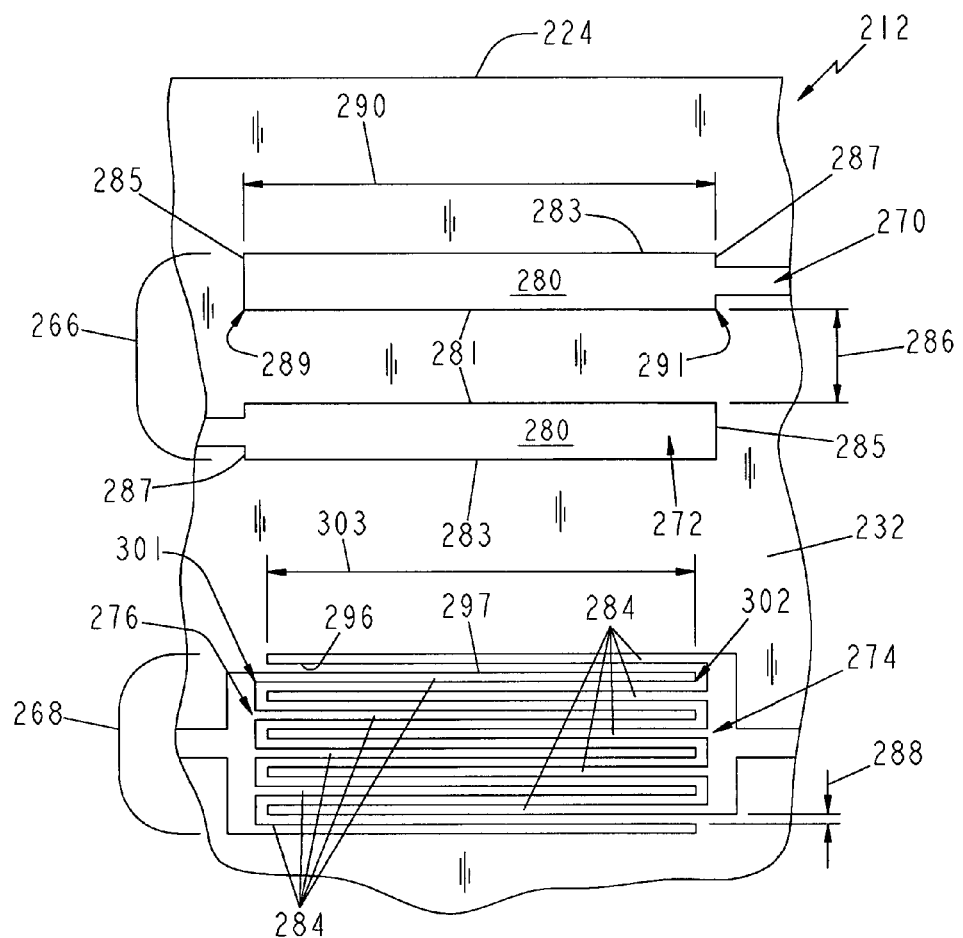
FIG. 3 illustrates an enlarged plan view of the biosensor of FIG. 1 showing a macroelectrode array and a microelectrode array.

Referring now to FIG. 3, the first electrode set 266 of the electrode system includes two electrodes 270, 272. Illustratively, electrode 270 is a working electrode and electrode 272 is a counter electrode. The electrodes 270, 272 each have a single element or finger 280 that is in communication with a contact pad 278 via a connecting trace 279 (shown in FIG. 2). The electrode fingers 280 of the electrodes 270, 272 cooperate to define an electrode pattern formed as a macroelectrode array. It is appreciated, as will be discussed hereafter, that the electrodes 270, 272 can include more than one finger each in accordance with this disclosure. It is further appreciated that the shape, size and relative configuration of the electrodes fingers may vary in accordance with the present disclosure.

As shown in FIG. 2, the second electrode set 268 includes two electrodes 274, 276. Illustratively, electrode 274 is a working electrode and electrode 276 is a counter electrode. Further, the electrodes 274, 276 each have five electrode elements or fingers 284 that are in communication with a contact pad 282 via a connecting trace 277. Referring now to FIG. 3, the electrode fingers 284 cooperate to define an electrode pattern formed as an interlaced microelectrode array. While five electrode fingers 284 are illustrated, it is appreciated that the elements of electrodes 274, 276 can each be formed with greater or fewer than five electrode fingers in accordance with this disclosure. It is further appreciated that the shape, size and relative configuration of the electrodes may vary in accordance with the present disclosure.

It is appreciated that the values for the dimensions of the electrode sets 266, 268 as illustrated in FIG. 2 are for a single specific embodiment, and these values may be selected as needed for the specific use. For example, the length of the electrode sets may be any length, up to the length of the base depending upon the orientation of the electrode sets on the base. Further, it is appreciated that the width of the conducting traces in communication with the electrode sets may vary, a non-limiting example of which is from about 0.4 mm to about 5 mm. It is further appreciated that the width of each contact pad may vary, a non-limiting example of which is from about 1 mm to about 5 mm. The electrode patterns shown in FIG. 2 are symmetric, however this is not required, and irregular or asymmetric patterns (or electrode shapes) are possible in accordance with this disclosure. Further, the number of electrode sets on the base 212 may vary, and therefore each base 212 can contain, for example 1 to 1000 electrode sets, preferably 2 to 20 electrode sets, more preferably 2 to 3 electrode sets.

Referring again to the first electrode set 266 of FIG. 3, each electrode finger 280 is defined by an inner edge 281, an outer edge 283, and opposite third and fourth edges 285, 287. Each edge 218, 283, 285, 287 has a smooth edge quality. As discussed earlier, the edge quality of the electrodes 270, 272 is defined by the edge's deviation from a line extending between first and second points. The following description of deviations can apply to each edge of electrodes 270, 272 of biosensor 210. For clarity purposes, however, only the edge 281 of electrode 270 will be discussed hereafter.

As shown in FIG. 3, the edge 281 of electrode 270 extends between points 289, 291 located on the base 212. For illustrative purposes only, points 289, 291 are located at opposite ends of the inner edge 281. It is appreciated that the points 289, 291 may be positioned at a variety of locations and at a variety of distances relative to one another depending upon the length of the desired edge in accordance with this disclosure.

Figure 4:
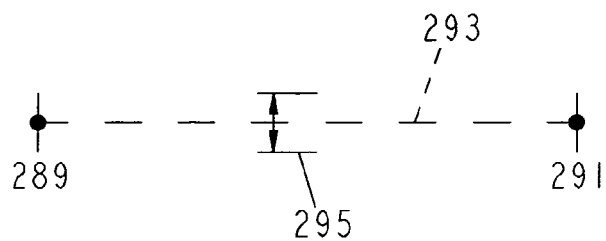
FIG. 4 illustrates a diagram of an edge deviation from a line.
Figure 10:
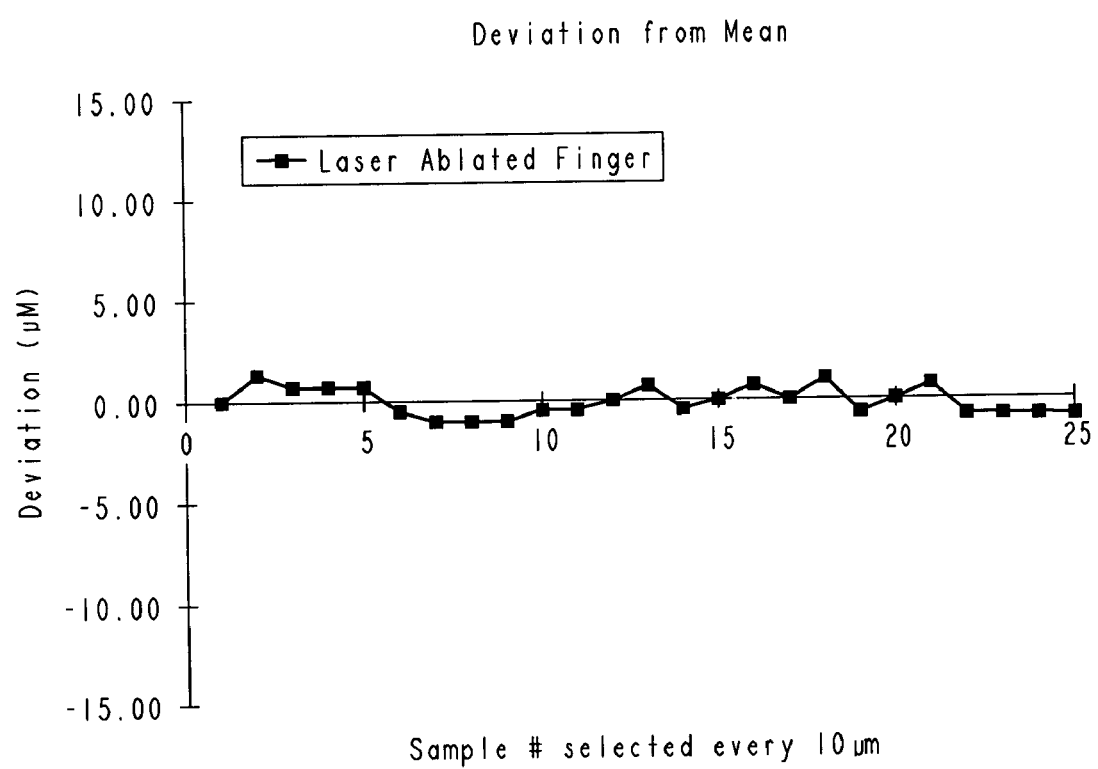
FIG. 10 illustrates a graph showing a deviation from mean of an electrode edge of the microelectrode array of FIG. 3.

As shown in FIG. 4, a line 293 extends exactly between points 289, 291. A standard deviation of the edge 281 (as shown by arrow 295) from the line 293 is less than about 6 µm in accordance with this disclosure, creating an edge with a smooth edge quality. In preferred embodiments, the standard deviation of the edge from the line 293 is less than 2 µm, and most preferably less than 1.0 µm. An example of this deviation from mean is illustrated in FIG. 10. Further, a photograph of an edge with a smooth edge quality is shown in FIG. 22.

The edge quality illustrated in FIG. 10 was measured using Micro-Measure system commercially available from LPKF Laser Electronic GmbH, of Garbsen, Germany with Metric 6.21 software. The Metric software allows the display and measuring of video images on the PC. Measurements were made by capturing the image and then allowing the software to place a 10 µm grid over the image. Measurements of the width were made at 10 µm intervals along the length of a line 250 µm using a point-to-point process. The effective video magnification to video screen was 575×. (Using objective Q750). Video magnification=Actual measured "Scale length" on the video screen (µm)/Scale value (µm). For example, 115000 µm/200 µm=575×.

Figure 21:
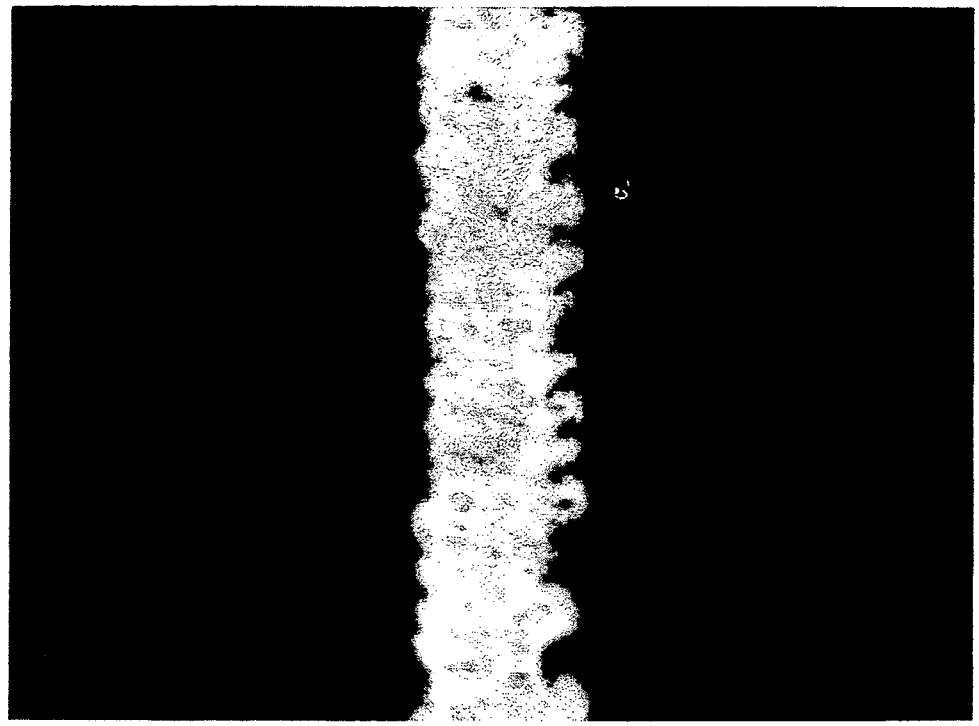
FIG. 21 is a microscopic view of a portion of an electrical component having a rough edge.

Further, the deviation from mean of the edges illustrated photographically by FIGS. 21 and 22 was measured using a QVH-606 PRO Vision Measuring System (computer-controlled non-contact measurement system), commercially available from Mitutoyo America Corporation, Aurora, Ill. with an effective magnification to video screen=470×. Standard deviations were calculated from measurements made at an average interval of 0.69 µm for a length of at least 250 µm. Other settings: Ring lighting (Intensity 89, Position 60), Edge Detection (Edge Slope=Falling, Edge Detection TH=169, THS=18.5, THR=0.5 Scan Interval=1). The deviation from mean of the edge of FIG. 21 was plotted and found to be greater than 6 µm. Referring to FIG. 22, the deviation from mean was plotted for the edge and found to be less than about 2 µm.

Referring again to FIG. 4, the line 293 is illustratively a straight line. It is appreciated, however, that the shape of the line 293 is unimportant as it may be curved or angular, so long as the standard deviation of the edge 281 from that line 293 is less than about 6 μm. It is also appreciated, as discussed above, that the specific positions of first and second locations 289, 291 on the surface 232 may vary in accordance with the disclosure depending upon the desired length of the electrode edge.

The electrode fingers 280, as shown in FIG. 3, are separated from one another by an electrode gap 286, which corresponds to the feature size of the electrode pattern of the electrode set 266. The electrode gap 286 relates to the smallest dimension of space between the adjacent edges 281 of electrode fingers 280. Illustratively, in biosensor 210, the electrically insulative material of the top surface 232 is exposed between the electrode fingers 280 along a length 290. It is appreciated, however, that rather than top surface 232 being exposed, the base can be coated with materials, or recesses can be formed between the electrodes as disclosed in U.S. patent application Ser. No. 09/704,145, filed on Nov. 1, 2000, the disclosure of which is incorporated herein by reference.

Figure 5:
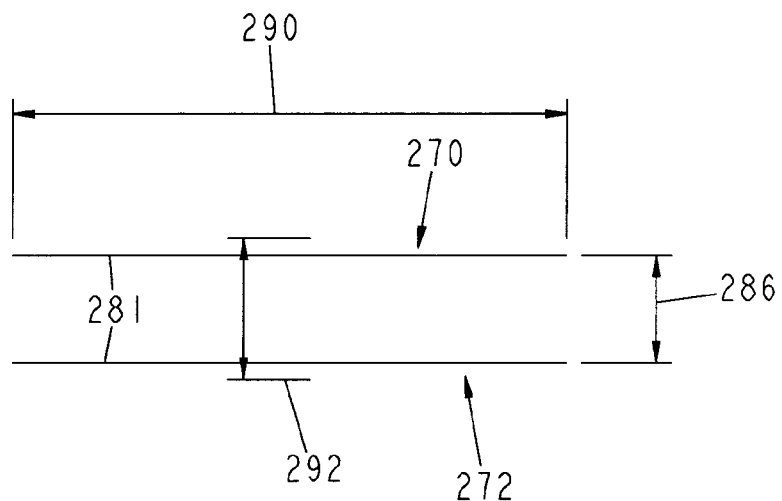
FIG. 5 illustrates a diagram of a gap deviation from a pre-defined width value for the gap.

As shown in FIGS. 3 and 5, the inner edges 281 of electrode fingers 280 have an equal length, illustrated by the numeral 290 and are separated from one another by the electrode gap 286. Illustratively, the electrode gap 286 has a width of about 100 μm to about 250 μm, more specifically the width is about 250 μm. As shown in FIG. 3, the gap 286 has a pre-determined width value along a length 290 of the opposing edges 281 of the electrode fingers 280. A standard deviation (as shown by arrow 292 in FIG. 5) of the gap 286 from the width value is less than 6 μm, preferably less than 2 μm, and most preferably less than 1.0 μm. Further, the smoothness standard deviation for macroelectrodes is preferably less than about 2% of the gap between adjacent macroelectrode elements, more preferably less than about 1% of the gap 286.

Figure 6:
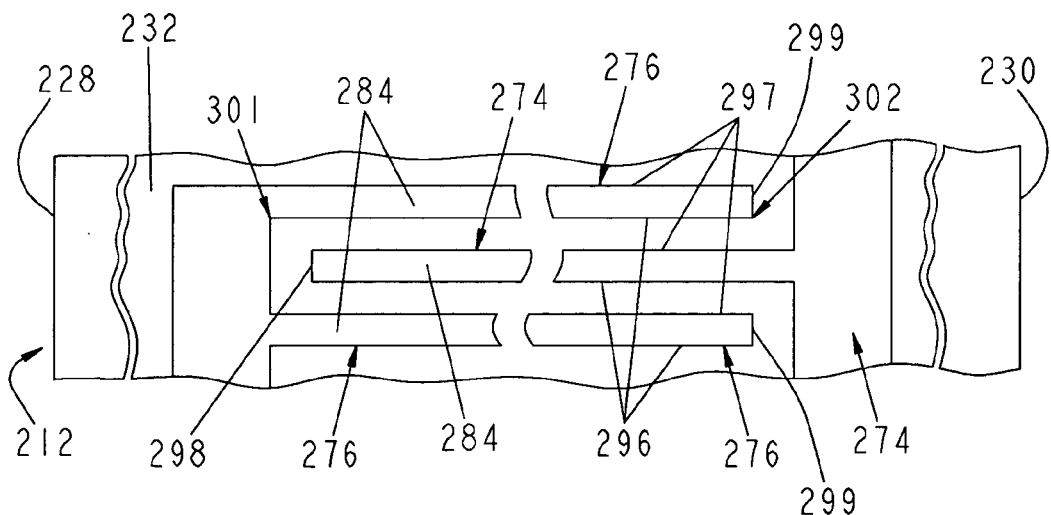
FIG. 6 illustrates an enlarged section of the microelectrode array of FIG. 3.

The electrode fingers 284, which define the elements of electrodes 274, 276 are illustrated in FIGS. 3 and 6. For clarity purposes, however, only three of these electrode fingers 284 will be discussed hereafter as they are illustrated in FIG. 6. Each electrode finger 284 is defined by a first edge 296 and a second edge 297. Further, adjacent fingers 284 have spaced-apart third and fourth edges 298, 299 respectively. These edges 296, 297, 298, 299 of fingers 284 can also have a smooth edge quality. As previously described with reference to electrodes 270, 272, the edge quality of the electrodes 274, 276 is defined by the respective edge's deviation from a line extending between first and second points. The following description of deviations will apply to each edge of electrode fingers 284 of biosensor 210. For clarity purposes, however, only one edge 296 of electrode finger 284 will be discussed hereafter.

Figure 7:
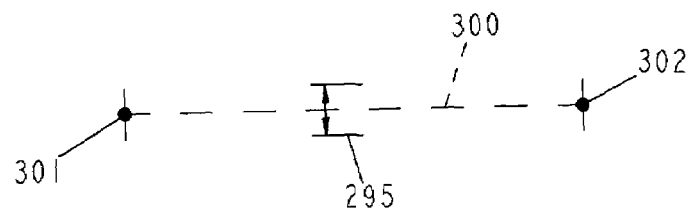
FIG. 7 illustrates a diagram of an edge deviation from a line.

The edge 296 of electrode finger 284 extends between first and second points 301, 302 located on the base 212. As shown in FIG. 7, a line 300 extends exactly between points 301, 302. A standard deviation of the edge 296 (as shown by arrow 295) from the line 300 is less than about 6 μm, in accordance with this disclosure, creating an edge with a smooth edge quality. In preferred embodiments, the standard deviation of the edge from the line 300 is less than 2 μm, and most preferably less than 1.0 μm. Illustratively, the line 300 is a straight line. It is appreciated, however, that the shape of the line 300 is unimportant as it may be curved or angular. It is also appreciated that the specific positions of first and second locations 300, 301 on the surface 232 may vary in accordance with the disclosure.

Referring again to FIG. 3, the electrode fingers 284 are separated from one another by an electrode gap 288, which corresponds to the feature size of the electrode pattern of the electrode set 268. The electrode gap 288 relates to the smallest dimension of space between adjacent edges 296, 297 of fingers 284. Illustratively, in biosensor 210, the electrically insulative material of the base 212 is exposed between the electrode fingers 284 along a length 303. It is appreciated, however, that rather than top surface 232 being exposed, the base can be coated with materials, or recesses can be formed between the electrodes as disclosed in U.S. patent application Ser. No. 09/704,145, filed on Nov. 1, 2000 and entitled "Biosensor", the disclosure of which is incorporated herein by reference.

The electrode gap 288, which corresponds to the feature size of the electrode pattern of the electrode set 268 is different than the feature size of the electrode pattern of the electrode set 266. Illustratively, the feature size, or gap 288 between the electrode fingers 284 has a width of about 100 μm or less, including about 1 μm to about 100 μm, even more preferably 75 μm or less, including about 17 μm to about 50 μm. It is appreciated that the electrode gap for a microelectrode array can vary. For example, it is understood that the electrode gap can be less than 1 μm in accordance with the present disclosure. The size of the achievable gap is dependent upon the quality of the optics, the wavelength of the laser, and the window size of a mask field.

As illustrated in FIG. 3, the gap 288 has a pre-determined width value along a length 303 of the opposing edges 296, 297 of the electrode fingers 284. A standard deviation of the gap 288 from the width value is less than 6 μm, preferably less than 2 μm, and most preferably less than 1.0 μm. It is appreciated that if the microelements are spaced apart by less than 2 μm, then the smoothness standard deviation is preferably less than one half, and more preferably less than one fourth, the feature size of the microelement pattern. In general, the smoothness standard deviation for microelectrodes is preferably less than about 5% of the gap between adjacent microelements or feature size, more preferably less than about 2% of the gap or feature size.

Referring now to FIG. 9, the electrode fingers 284 are covered with the reagent 264 and may be used to provide electrochemical probes for specific analytes. The starting reagents are the reactants or components of the reagent, and are often compounded together in liquid form before application to the ribbons or reels, or in capillary channels on sheets of electrodes. The liquid may then evaporate, leaving the reagent in solid form. The choice of a specific reagent depends on the specific analyte or analytes to be measured, and is not critical to the present invention. Various reagent compositions are well known to those of ordinary skill in the art. It is also appreciated that the placement choice for the reagent on the base may vary and depends on the intended use of the biosensor. Further, it is appreciated that the techniques for applying the reagent onto the base may vary, for example it is within the scope of the present disclosure to have the reagent screen-printed onto the fingers.

A non-limiting example of a dispensable reagent for measurement of glucose in a human blood sample contains 62.2 mg polyethylene oxide (mean molecular weight of 100–900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is further described in U.S. Pat. No. 5,997,817, the disclosure of which is expressly incorporated herein by reference.

A non-limiting example of a dispensable reagent for measurement of hematocrit in a sample contains oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is expressly incorporated herein by reference.

Non-limiting examples of enzymes and mediators that may be used in measuring particular analytes in biosensors of the present invention are listed below in Table 1.

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensors in accordance with this disclosure.

Another non-limiting example of a suitable dispensable reagent for use with biosensors of the present invention is nitrosoanaline reagent, which includes a PQQ-GDH and para-Nitroso-Aniline mediator. A protocol for the preparation of the nitrosoanaline reagent is the same in all respects as disclosed in U.S. patent application Ser. No. 10/688,312 entitled "System And Method For Analyte Measurement Using AC Excitation", filed simultaneously herewith, the disclosure of which is incorporated herein by reference. The reagent mass composition—prior to dispensing and drying is as set forth in Table 2.

TABLE 1

| Analyte | Enzymes | Mediator (Oxidized Form) | Additional Mediator |
|---|---|---|---|
| Glucose | Glucose Dehydrogenase and Diaphorase | Ferricyanide | Osmium complexes, nitrosoanaline complexes |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

TABLE 2

| | Component | % w/w | Mass for 1 kg |
|---|---|---|---|
| solid | Polyethylene oxide (300 KDa) | 0.8054% | 8.0539 g |
| solid | NATROSOL ® 250 M | 0.0470% | 0.4698 g |
| solid | AVICEL ® RC-591F | 0.5410% | 5.4104 g |
| solid | Monobasic potassium phosphate (anhydrous) | 1.1437% | 11.4371 g |
| solid | Dibasic potassium phosphate (anhydrous) | 1.5437% | 15.4367 g |
| solid | Sodium Succinate hexahydrate | 0.5876% | 5.8761 g |
| solid | Potassium Hydroxide | 0.3358% | 3.3579 g |
| solid | Quinoprotein glucose dehydrogenase (EncC#: 1.1.99.17) | 0.1646% | 1.6464 g |
| solid | PQQ | 0.0042% | 0.0423 g |
| solid | Trehalose | 1.8875% | 18.8746 g |
| solid | Mediator BM 31.1144 | 0.6636% | 6.6363 g |
| solid | TRITON ® X-100 | 0.0327% | 0.3274 g |
| solvent | Water | 92.2389% | 922.3888 g |

Figure 17:
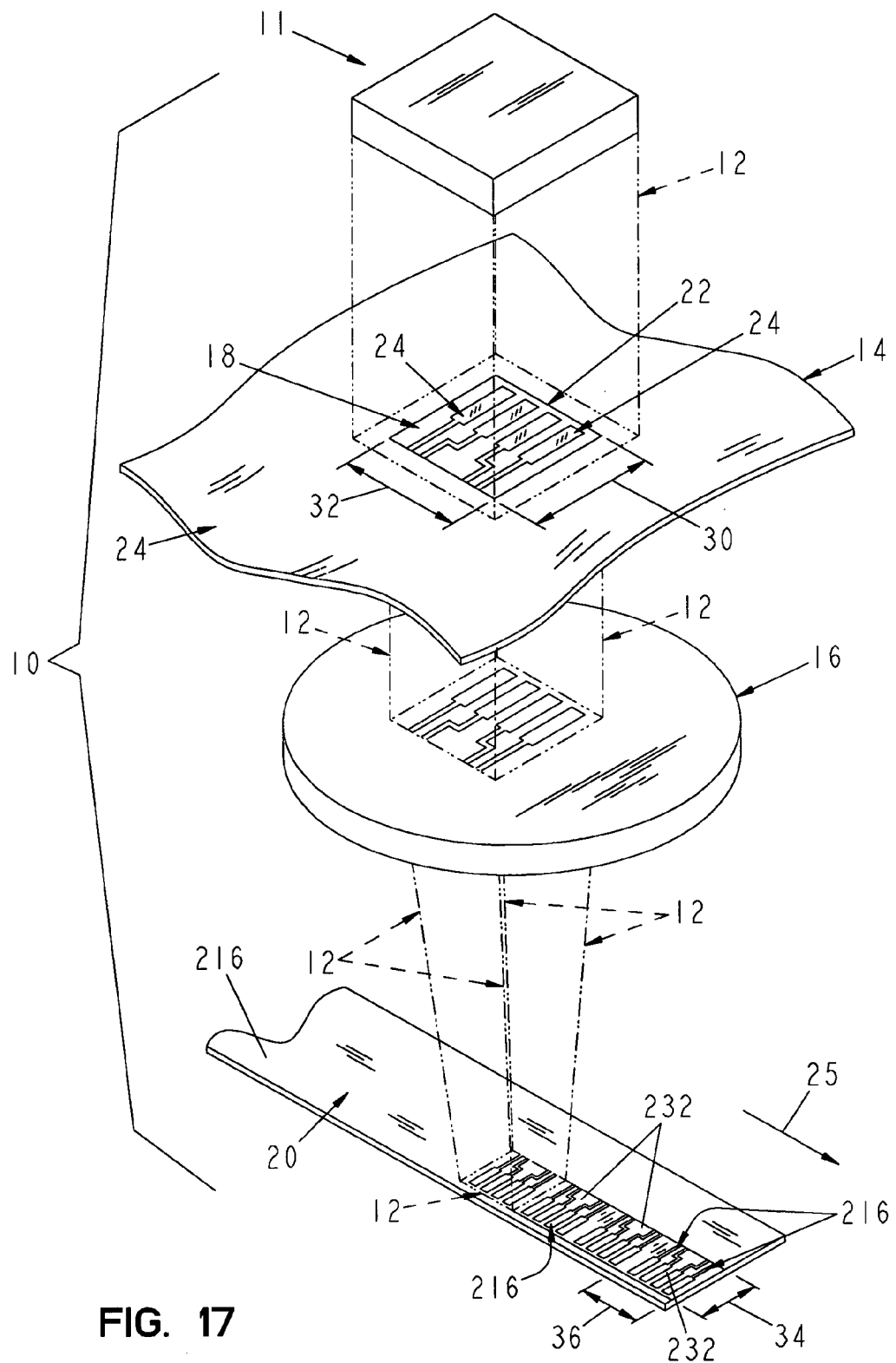
FIG. 17 illustrates a view of an ablation apparatus suitable for use with the present invention.
Figure 18:
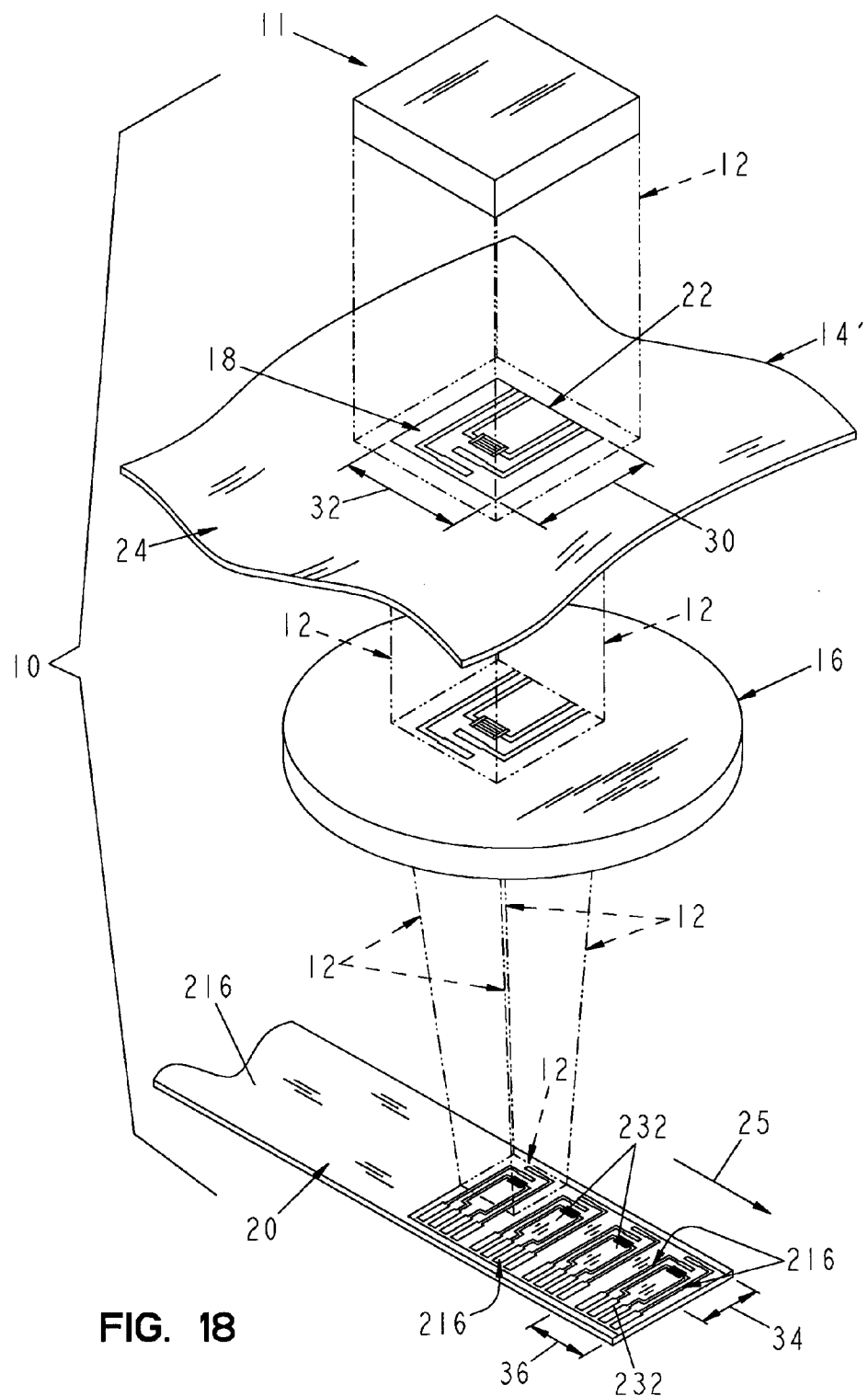
FIG. 18 is a view of the laser ablation apparatus of FIG. 17 showing a second mask.
Figure 19:
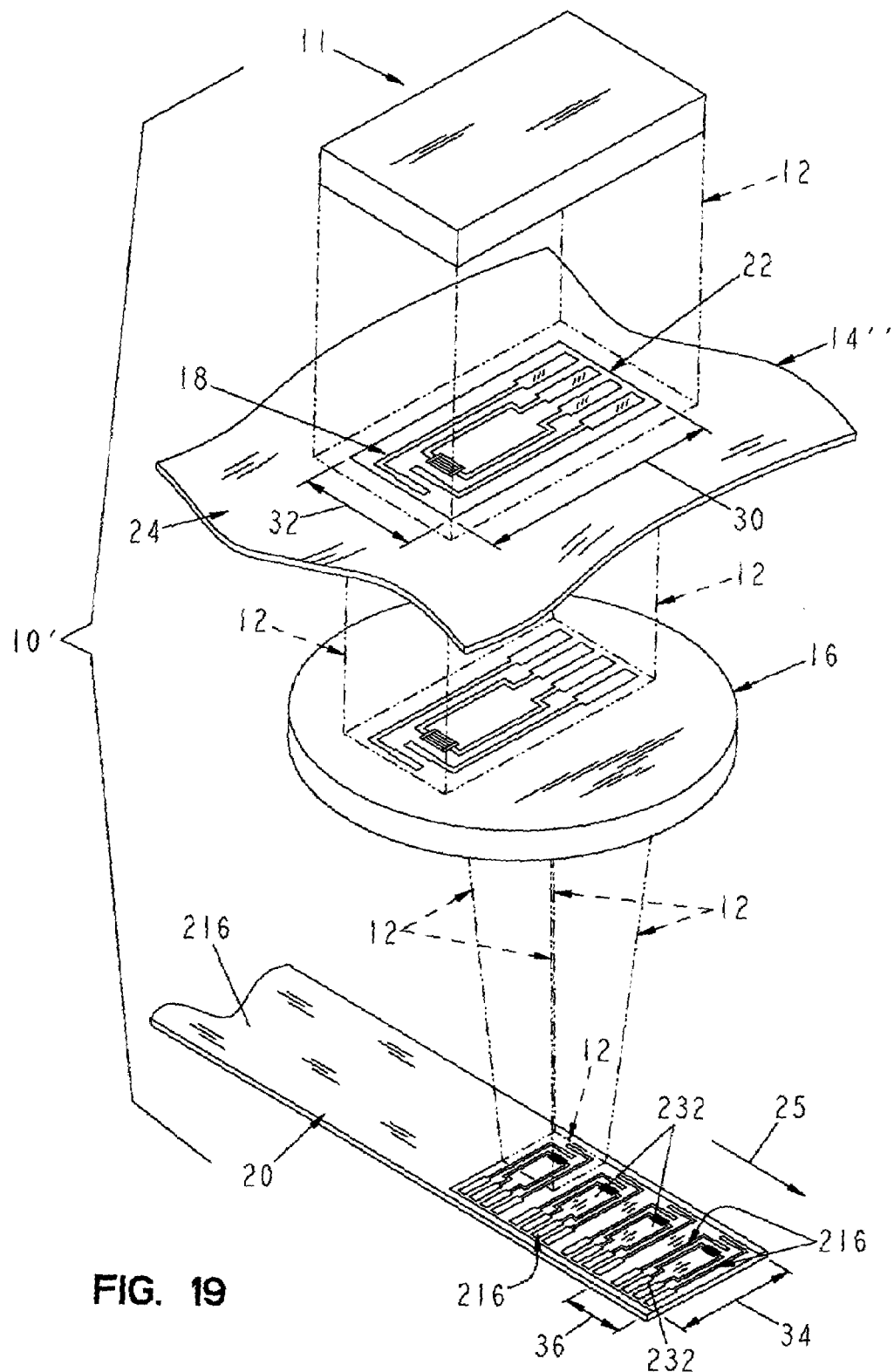
FIG. 19 is a view of an ablation apparatus suitable for use with the present invention.

% Solids 0.1352687
Target pH 6.8
Specific Enzyme Activity Used (U/mg 689 DCIP
Dispense Volume per Biosensor 4.6 mg Biosensor 210 is illustratively manufactured using two apparatuses 10, 10', shown in FIGS. 17–18 and 19, respectively. It is appreciated that unless otherwise described, the apparatuses 10, 10' operate in a similar manner. Referring first to FIG. 17, biosensor 210 is manufactured by feeding a roll of ribbon 20 having an 80 nm gold laminate, which is about 40 mm in width, into a custom fit broad field laser ablation apparatus 10. The apparatus 10 comprises a laser source 11 producing a beam of laser light 12, a chromium-plated quartz mask 14, and optics 16. It is appreciated that while the illustrated optics 16 is a single lens, optics 16 is preferably a variety of lenses that cooperate to make the light 12 in a pre-determined shape.

A non-limiting example of a suitable ablation apparatus 10 (FIGS. 17–18) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Göttingen, Germany and a chromium-plated quartz mask commercially available from International Phototool Company, Colorado Springs, Colo.

For the MicrolineLaser 200-4 laser system (FIGS. 17–18), the laser source 11 is a LPX-200 KrF-UV-laser. It is appreciated, however, that higher wavelength UV lasers can be used in accordance with this disclosure. The laser source 11 works at 248 nm, with a pulse energy of 600 mJ, and a pulse repeat frequency of 50 Hz. The intensity of the laser beam 12 can be infinitely adjusted between 3% and 92% by a dielectric beam attenuator (not shown). The beam profile is 27×15 mm² (0.62 sq. inch) and the pulse duration 25 ns. The layout on the mask 14 is homogeneously projected by an optical elements beam expander, homogenizer, and field lens (not shown). The performance of the homogenizer has been determined by measuring the energy profile. The imaging optics 16 transfer the structures of the mask 14 onto the ribbon 20. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 20 moves as shown by arrow 25 to allow a number of layout segments to be ablated in succession.

The positioning of the mask 14, movement of the ribbon 20, and laser energy are computer controlled. As shown in FIG. 17, the laser beam 12 is projected onto the ribbon 20 to be ablated. Light 12 passing through the clear areas or windows 18 of the mask 14 ablates the metal from the ribbon 20. Chromium coated areas 24 of the mask 14 blocks the laser light 12 and prevent ablation in those areas, resulting in a metallized structure on the ribbon 20 surface. Referring now to FIG. 18, a complete structure of electrical components may require additional ablation steps through a second mask 14'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 10' (FIG. 19) is a customized laser system commercially available from LPKF Laser Electronic GmbH, of Garbsen, Germany, which incorporates a Lambda STEEL (Stable energy eximer laser) laser system commercially available from Lambda Physik AG, Göttingen, Germany and a chromium-plated quartz mask commercially available from International Phototool Company, Colorado Springs, Colo. The laser system features up to 1000 mJ pulse energy at a wavelength of 308 nm. Further, the laser system has a frequency of 100 Hz. The apparatus 10' may be formed to produce biosensors with two passes as shown in FIGS. 17 and 18, but preferably its optics permit the formation of a 10×40 mm pattern in a 25 ns single pass, or a single pulse of a laser beam from the laser apparatus.

While not wishing to be bound to a specific theory, it is believed that the laser pulse or beam 12 that passes through the mask 14, 14', 14" is absorbed within less than 1 μm of the surface 232 on the ribbon 20. The photons of the beam 12 have an energy sufficient to cause photo-dissociation and the rapid breaking of chemical bonds at the metal/polymer interface. It is believed that this rapid chemical bond breaking causes a sudden pressure increase within the absorption region and forces material (metal film 216) to be ejected from the polymer base surface. Since typical pulse durations are around 20–25 nanoseconds, the interaction with the material occurs very rapidly and thermal damage to edges of the conductive material 216 and surrounding structures is minimized. The resulting edges of the electrical components have high edge quality and accurate placement as contemplated by the present invention.

Fluence energies used to remove or ablate metals from the ribbon 20 are dependent upon the material from which the ribbon 20 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm², on polyimide about 100 to about 120 mJ/cm², and on MELINEX® about 60 to about 120 mJ/cm². It is understood that fluence levels less than or greater than the above mentioned can be appropriate for other base materials in accordance with the disclosure.

Patterning of areas of the ribbon 20 is achieved by using the masks 14, 14'. Each mask 14, 14' illustratively includes a mask field 22 containing a precise two-dimensional illustration of a pre-determined portion of the electrode component patterns to be formed. FIG. 17 illustrates the mask field 22 including contact pads and a portion of traces. As shown in FIG. 18, the second mask 14' contains a second corresponding portion of the traces and the electrode patterns containing fingers. As previously described, it is appreciated that depending upon the size of the area to be ablated, the mask 14 can contain a complete illustration of the electrode patterns (FIG. 19), or portions of patterns different from those illustrated in FIGS. 17 and 18 in accordance with this disclosure. Preferably, it is contemplated that in one aspect of the present invention, the entire pattern of the electrical components on the test strip are laser ablated at one time, i.e., the broad field encompasses the entire size of the test strip (FIG. 19). In the alternative, and as illustrated in FIGS. 17 and 18, portions of the entire biosensor are done successively.

While mask 14 will be discussed hereafter, it is appreciated that unless indicated otherwise, the discussion will apply to masks 14', 14" as well. Referring to FIG. 17, areas 24 of the mask field 22 protected by the chrome will block the projection of the laser beam 12 to the ribbon 20. Clear areas or windows 18 in the mask field 22 allow the laser beam 12 to pass through the mask 14 and to impact predetermined areas of the ribbon 20. As shown in FIG. 17, the clear area 18 of the mask field 22 corresponds to the areas of the ribbon 20 from which the conductive material 216 is to be removed.

Further, the mask field 22 has a length shown by line 30 and a width as shown by line 32. Given the imaging ratio of 2:1 of the LPX-200, it is appreciated that the length 30 of the mask is two times the length of a length 34 of the resulting pattern and the width 32 of the mask is two times the width of a width 36 of the resulting pattern on ribbon 20. The optics 16 reduces the size of laser beam 12 that strikes the ribbon 20. It is appreciated that the relative dimensions of the mask field 22 and the resulting pattern can vary in accordance with this disclosure. Mask 14' (FIG. 18) is used to complete the two-dimensional illustration of the electrical components.

Continuing to refer to FIG. 17, in the laser ablation apparatus 10 the excimer laser source 11 emits beam 12, which passes through the chrome-on-quartz mask 14. The mask field 22 causes parts of the laser beam 12 to be reflected while allowing other parts of the beam to pass through, creating a pattern on the gold film where impacted by the laser beam 12. It is appreciated that ribbon 20 can be stationary relative to apparatus 10 or move continuously on a roll through apparatus 10. Accordingly, non-limiting rates of movement of the ribbon 20 can be from about 0 m/min to about 100 m/min, more preferably about 30 m/min to about 60 m/min. It is appreciated that the rate of movement of the ribbon 20 is limited only by the apparatus 10 selected and may well exceed 100 m/min depending upon the pulse duration of the laser source 11 in accordance with the present disclosure.

Once the pattern of the mask 14 is created on the ribbon 20, the ribbon is rewound and fed through the apparatus 10 again, with mask 14' (FIG. 18). It is appreciated, that alternatively, laser apparatus 10 could be positioned in series in accordance with this disclosure. A detailed description of the step and repeat process is found in U.S. application Ser. No. 60/480,397, filed simultaneously herewith, entitled "Devices And Methods Relating To Analyte Sensors", the disclosure of which is incorporated herein by reference. Thus, by using masks 14, 14', large areas of the ribbon 20 can be patterned using step-and-repeat processes involving multiple mask fields 22 in the same mask area to enable the economical creation of intricate electrode patterns and other electrical components on a substrate of the base, the precise edges of the electrode components, and the removal of greater amounts of the metallic film from the base material.

Figure 20:
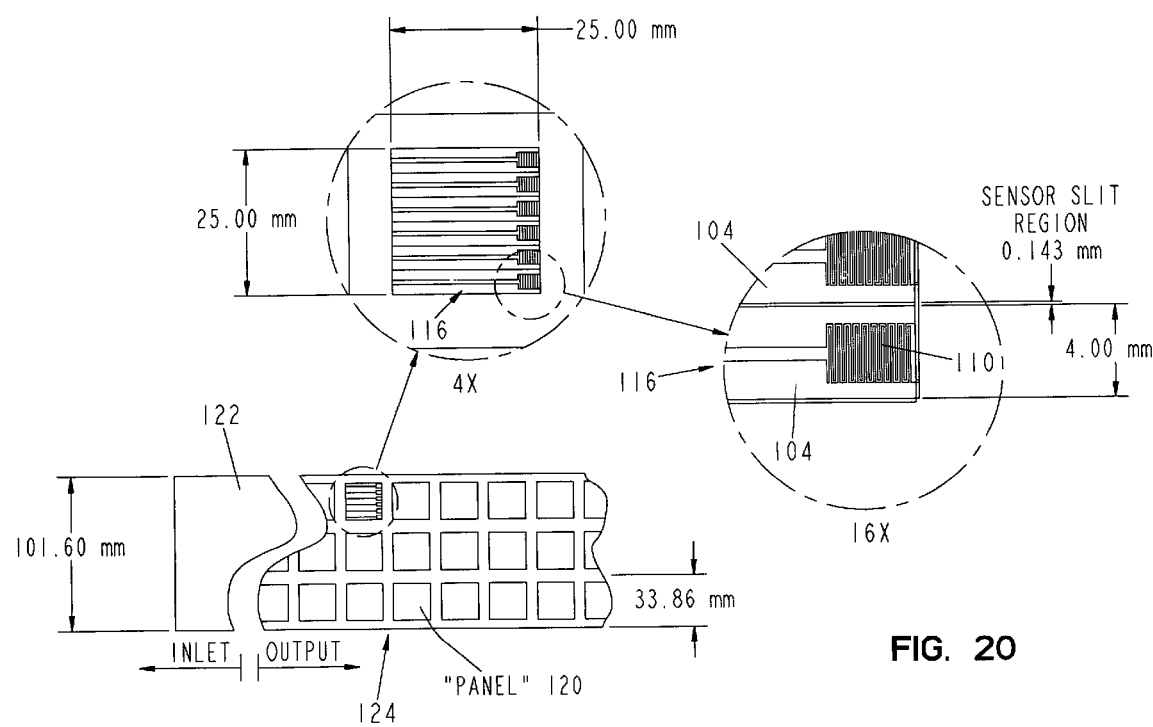
FIG. 20 is a schematic of an electrode set ribbon of the present invention.

FIG. 20 is a non-limiting schematic of an electrode set ribbon 124 formed in accordance with the present disclosure, although having an electrode pattern different from that illustrated in FIGS. 17 and 18. The ribbon 124 includes a plurality of panels 120, each of which includes a plurality of electrode systems 116. Each system includes two electrodes 104 and 104 having a sensing region 110. Also shown is the original metallic laminate ribbon 122 that is subject to laser ablation to form the electrode set ribbon 124. The width of the ribbon 122 is selected to accommodate the laser ablation system 10, 10', and may be, for example, 40 to 0.4 inches (1.2 m to 10.25 mm). The ribbon may be any length, and is selected based on the desired number of electrode sets, and/or the ease of handling and transport of the ribbons. The size of each individual panel is selected to fit conveniently on the ribbon, and therefore each panel may contain 1 to 1000 electrode sets, preferably 2 to 20 electrode sets.

Once the complete electrode patterns are created, it is appreciated that the ribbon 20 may be coupled to a spacer and a cover using any number of well-known commercially available methods. A non-limiting example of a suitable method of manufacture, is described in detail in U.S. application Ser. No. 60/480,397, filed simultaneously herewith, entitled "Devices And Methods Relating To Analyte Sensors", the disclosure of which is incorporated herein by reference. In summary, however, it is appreciated that a reagent is placed upon the ribbon and dried conventionally with an in-line drying system. The rate of processing is nominally 30–38 meters per minute and depends upon the rheology of the reagent. Reagents suitable for the biosensor 210 are given above, but a preferable reagent is set out in Table 2.

The materials are processed in continuous reels such that the electrode pattern is orthogonal to the length of the reel, in the case of the base. The spacer material is laminated onto the coated ribbon 20. Prior to laminating the spacer material, however, a portion of the spacer material is removed, thereby forming a slit. A punching process is used to remove the unneeded portion of the spacer. The die set governs the shape of the slit. The resulting slit-spacer is placed in a reel-to-reel process onto the base. A cover is then laminated onto the spacer using a reel-to reel process. The biosensors can then be produced from the resulting reels of material by means of slitting and cutting.

The slit in the spacer preferably forms a capillary fill space between the base and the cover. A hydrophobic adhesive on the spacer prevents the test sample from flowing into the reagent under the spacer and therefore the fill space defines the test chamber volume. It is appreciated that the chamber volume can vary in accordance with this disclosure depending upon the application of the biosensor. A non-limiting detailed description of suitable fill volumes is found in U.S. application Ser. No. 60/480,397, filed simultaneously herewith, and entitled "Devices And Methods Relating To Analyte Sensors", the disclosure of which is incorporated herein by reference.

As discussed above, biosensor 210 has two electrode patterns having different feature sizes on a common planar surface and thus achieves multiple functionalities on that surface. Preferably, electrode set 266 has an electrode pattern formed as a macro electrode array with a first predefined feature size. A non-limiting example of a suitable functionality of the macroelectrode array is hematocrit level correction, which is described in U.S. patent application Ser. Nos. 10/688,312, filed simultaneously herewith, entitled "System And Method For Analyte Measurement Using AC Excitation" and "Devices And Methods Relating To Electrochemical Biosensors" respectively, the disclosures of which are incorporated herein by reference. It is appreciated that during use, a test meter (not shown) applies a voltage to one electrode and measures the current response at the other electrode to obtain a signal as described in U.S. application Ser. No. 10/688,312, filed herewith, entitled "System and Method For Analyte Measurement Using AC Excitation".

Electrode set 268 has an electrode pattern formed as an interlaced microelectrode array with a second pre-defined feature size. A non-limiting example of a suitable functionality of the microelectrode array is glucose estimation, which is also described in U.S. patent application Ser. No. 10/688,312, filed simultaneously herewith, entitled "System And Method For Analyte Measurement Using AC Excitation", the disclosure of which is incorporated herein by reference. Further, it is appreciated that during use, a test meter (not shown) applies a voltage to one electrode and measures the current response at the other electrode to obtain a signal as described in U.S. patent application Ser. No. 10/688,312, filed simultaneously herewith, entitled "System and Method For Analyte Measurement Using AC Excitation", the disclosure of which is incorporated herein by reference.

In operation, a user places their lanced finger at opening 221 of biosensor 210. A liquid sample (whole blood) flows from the finger into the opening 221. The liquid sample is transported via capillary action through the sample-receiving chamber 220 and across the fingers 280 of the element of the electrode set 266. Subsequently, the liquid sample flows through the sample-receiving chamber 220 toward vent 262 and into engagement with the reagent 264 situated upon the fingers 284 of the element of the electrode set 268. As discussed above, hematocrit correction values are determined from the interaction of the liquid sample with the fingers 280 and a glucose determination from the interaction of the liquid sample/reagent mixture with the fingers 284. While hematocrit and glucose determination functionalities are described with reference to biosensor 210, it is appreciated that the electrode patterns, may be used for a variety of functionalities in accordance with the present disclosure.

The processes and products described include disposable biosensors, especially for use in diagnostic devices. However, also included are electrochemical biosensors for non-diagnostic uses, such as measuring an analyte in any biological, environmental, or other, sample. In addition, it is appreciated that various uses and available functions of the biosensor may stand alone or be combined with one another in accordance with this disclosure.

As discussed below with reference to FIGS. 11–16, each of the disclosed biosensors operates from the standpoint of a user in a manner similar to that described above with reference from 210. In addition, like components of the biosensors are numbered alike.

Figure 11:
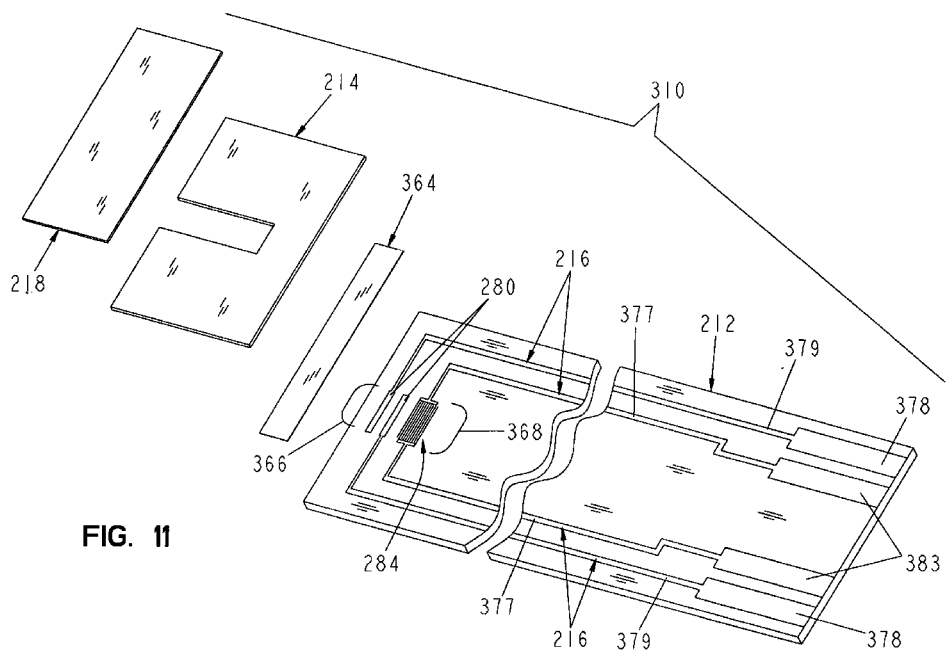
FIG. 11 illustrates an exploded assembly view of a biosensor in accordance with another embodiment of the invention.

Referring now to FIG. 11, a biosensor 310 is formed and manufactured in a manner similar to biosensor 210 except for the pattern of the conductive material 216 positioned on the base 212. The conductive material 216 of biosensor 310 defines a first electrode system 366 and a second electrode system 368. The electrode systems 366, 368 are similar to the systems of biosensor 210 except for the resulting pattern of the connecting traces 377, 379 and contact pads 378, 383 on the base 212. It is submitted that the traces 377, 379 and pads 378, 383 may take on a variety of shapes and sizes in accordance with this disclosure.

Figure 12:
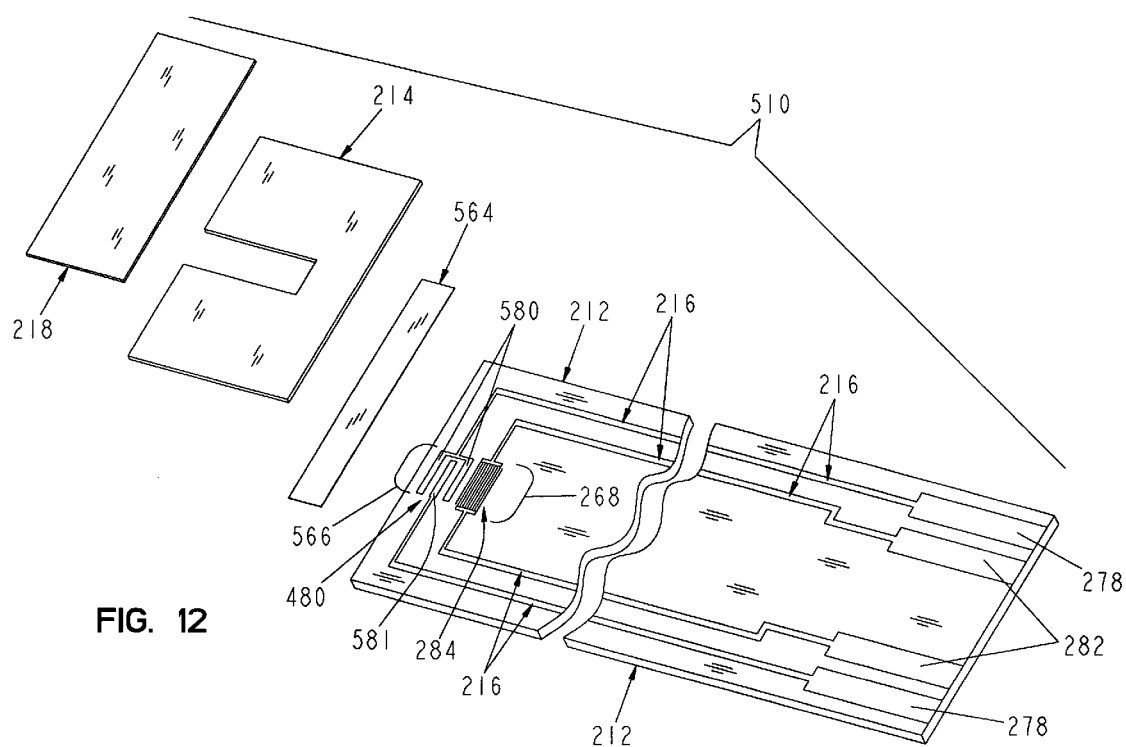
FIG. 12 illustrates an exploded assembly view of a biosensor in accordance with another embodiment of the invention.

As shown in FIG. 12, a biosensor 510 is formed in a manner similar to biosensor 210 except for the pattern of the conductive material 216 positioned on the base 212. In addition to electrode set 268, the conductive material 216 of biosensor 510 defines a first electrode set 566. The electrode set 566 is similar to set 366 except for the configuration of the interlacing electrode pattern formed by the elements of the electrodes.

Specifically, the first electrode set 566 includes a working electrode having an element with one electrode finger 581 and a counter electrode having a element with two electrode fingers 580. The fingers 580, 581 cooperate with one another to create an interlaced electrode pattern configured as a macroelectrode array having a feature size or gap width of about 250 μm. The electrodes 580, 581 each have an electrode width of about 250 μm. As discussed above with set 266, the electrode and gap widths may vary in accordance with this disclosure.

As described above with reference to biosensor 210, the first and second electrode sets 566, 268 have different feature sizes and are used to create different functionalities on biosensor 510. A non-limiting example of a suitable functionality of the first electrode set 566 is for determining correction factors for hematocrit levels. The measurement methods are as discussed above with reference to biosensor 210.

Figure 13:
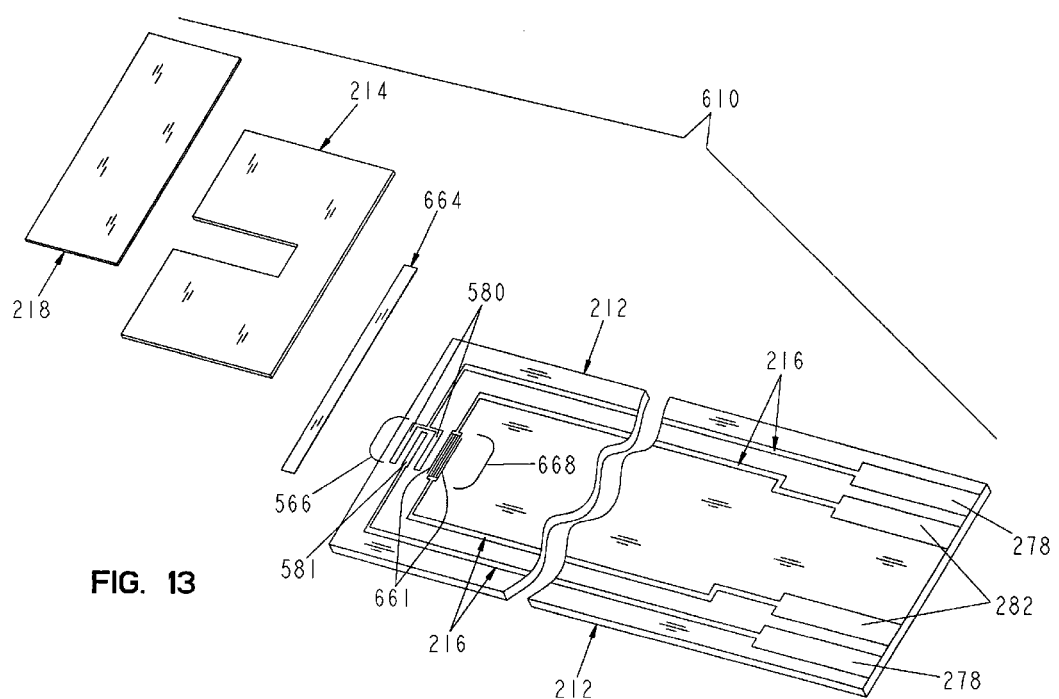
FIG. 13 illustrates an exploded assembly view of a biosensor in accordance with another embodiment of the invention.

Referring now to FIG. 13, a biosensor 610 is formed in a manner similar to biosensor 210 except for the pattern of the conductive material 216 positioned on the base 212. In addition to the first electrode set 566 as discussed above, the conductive material 216 of biosensor 610 defines a second electrode set 668 spaced-apart from set 566.

The electrode set 668 is similar to set 268 except for the pattern of interlacing electrode pattern in the element of the electrodes. Specifically, the second electrode set 668 includes a working electrode and a counter electrode, each having an element with three electrode fingers 661. The fingers 661 cooperate with one another to define an interlaced electrode pattern configured as a microelectrode array having a feature size or gap width of about 50 μm, which is less than the feature size of the electrode pattern of the set 566. The electrodes 661 each have an electrode width of about 50 μm. As discussed above with set 268, the electrode and gap widths may vary in accordance with this disclosure.

In addition, biosensor 610 includes a reagent 664. Reagent 664 is similar to reagent 264, and only differs in its width as it is applied onto the base 212. Specifically, the reagent 664 extends across electrode fingers 661. A non-limiting example of a suitable functionality of the second electrode set 668 is a glucose determination functionality. The measurement methods are as discussed above with reference to biosensor 210.

Figure 14:
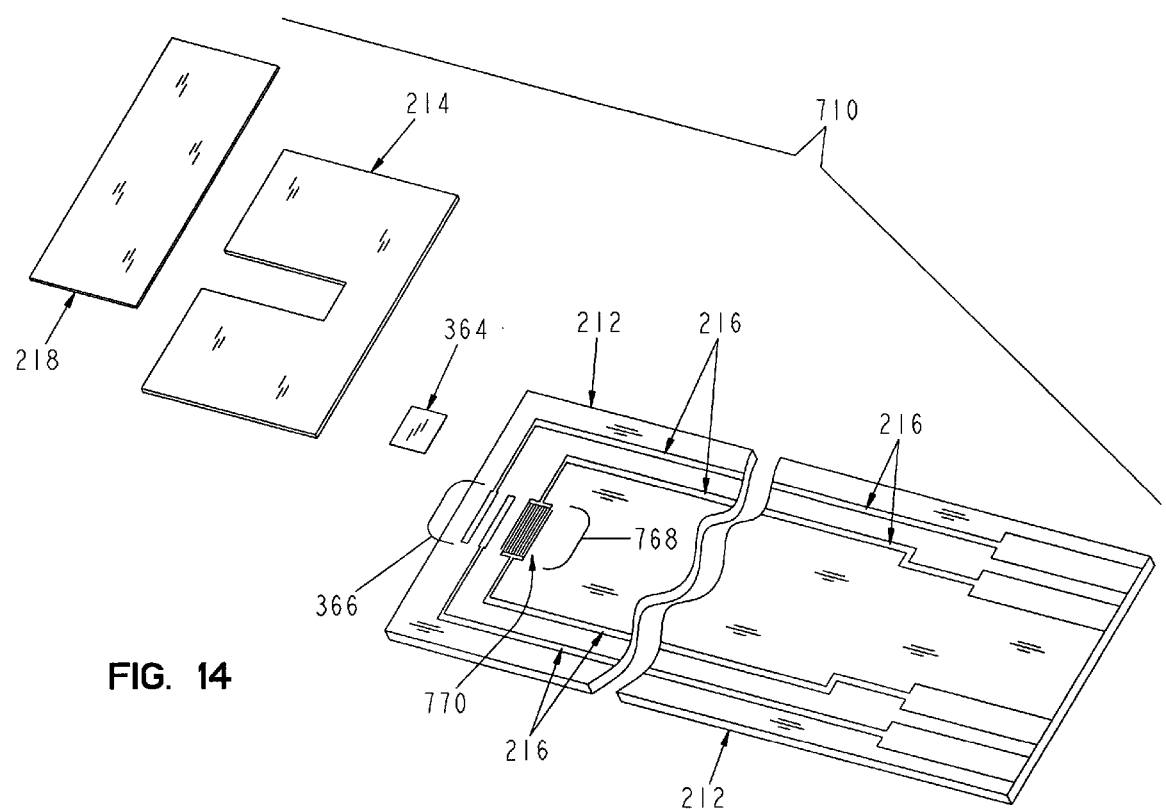
FIG. 14 illustrates an exploded assembly view of a biosensor in accordance with another embodiment of the invention.

As shown in FIG. 14, a biosensor 710 is formed in a manner similar to biosensor 210 except for the pattern of the conductive material 216 positioned on the base 212. The conductive material 216 of biosensor 710 defines the first electrode set 366 as discussed above and a second electrode set 768. The electrode set 768 is similar to set 268 except for the pattern of an interlacing electrode pattern formed by the element of the electrodes. Specifically, the second electrode set 768 includes a working electrode and a counter electrode, each having element with five electrode fingers 770. The fingers 770 cooperate with one another to define an interlaced electrode pattern configured as a microelectrode array having a feature size or gap width of about 30 μm, which is less than the feature size of electrode pattern of set 366. The electrode fingers 770 each have an electrode width of about 50 μm. As discussed above with set 266, the electrode and gap widths may vary in accordance with this disclosure. A non-limiting example of a suitable functionality of the second electrode set 668 is a glucose determination functionality. The measurement methods are as discussed above with reference to biosensor 210.

In addition, biosensor 710 includes a reagent 364 that is dispensed upon the fingers 770. It is appreciated that a variety of dispensing methods are well known to those skilled in the art. Reagent 364 is preferably the reagent set forth in Table 2. Moreover, it is appreciated that a variety of reagents, non-limiting examples of which have been discussed above, may be used in accordance with this disclosure.

Figure 15:
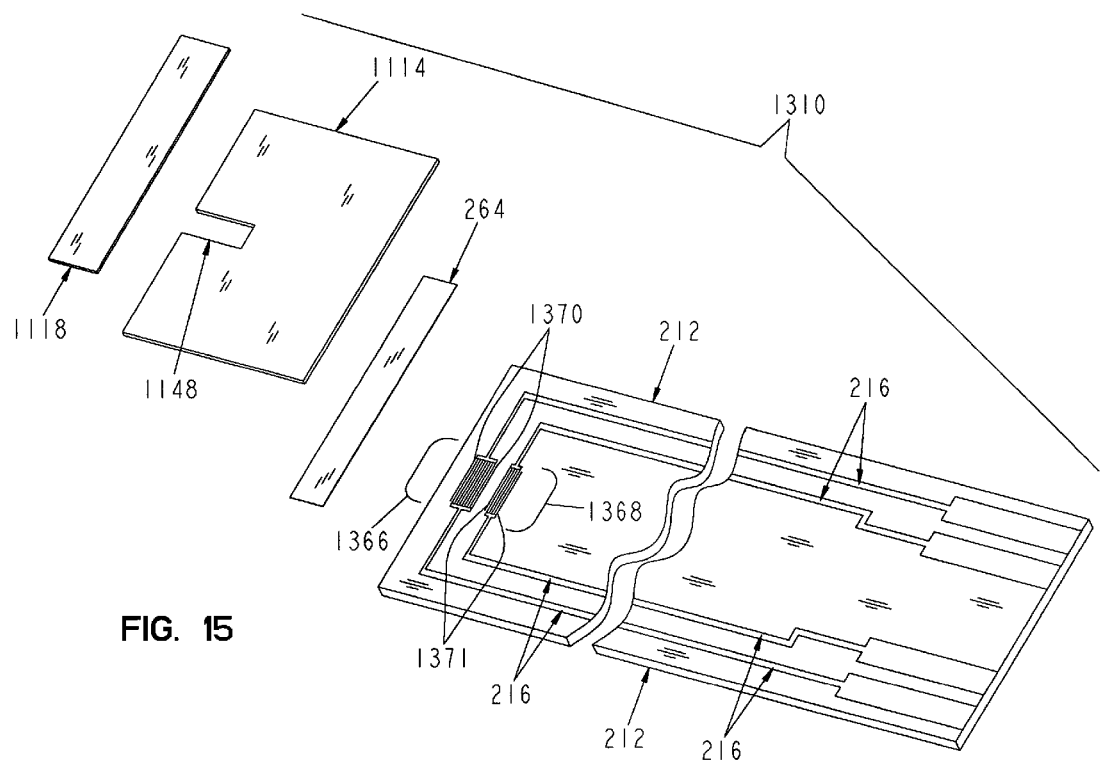
FIG. 15 illustrates an exploded assembly view of a biosensor in accordance with another embodiment of the invention.

FIG. 15 illustrates a biosensor 1310 in accordance with this disclosure. Biosensor 1310 is formed in a manner similar to biosensor 210 except for the configuration of the conductive material 216 positioned on the base 212, the cover 1118, and the spacer 1114. The cover 1118 and spacer 1114 are similar to cover 218 and spacer 214 except for their dimensions relative to the base 212 as shown in FIG. 15. The conductive material 216 of biosensor 1310 defines a first electrode set 1366 and a second electrode set 1368. The first electrode set 1366 includes a working electrode and a counter electrode, each having five electrode fingers 1370. The fingers 1370 cooperate with one another to define an interlaced electrode pattern formed as a microelectrode array having a feature size or gap width of about 17 μm. The electrode fingers 1370 each have an electrode width of about 20 μm.

The second electrode set 1368 includes a working electrode and a counter electrode, each having three electrode fingers 1371. The electrode fingers 1371 cooperate with one another to define an interlaced electrode pattern formed as a microelectrode array having a feature size or gap width of about 10 μm. The electrode fingers 1371 each have an electrode width of about 20 μm. As discussed above with set 266, the electrode and gap widths of fingers 1370 and 1371 may vary in accordance with this disclosure.

The reagent 264 extends across the electrode fingers 1371 of the electrode set 1368. A non-limiting example of a suitable functionality of the first electrode set 1366 includes hematocrit correction as described above with reference to biosensor 210.

Likewise, a non-limiting example of a suitable functionality of the second electrode set 1368 is used for determining a glucose estimate as described above with reference to biosensor 210. The method of measurement for the electrode sets, 1366 and 1368 is also as described above with reference to biosensor 210

Figure 16:
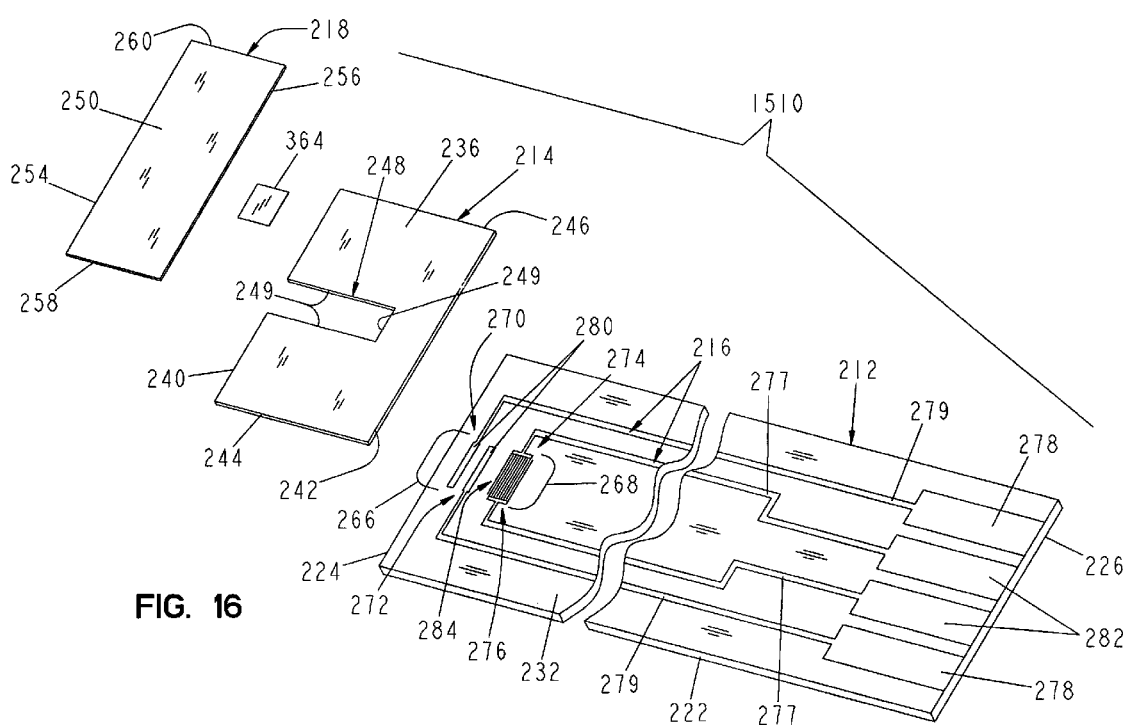
FIG. 16 illustrates an enlarged perspective view of a biosensor in accordance with another embodiment of the invention.

FIG. 16 illustrates biosensor 1510. Biosensor 1510 is identical to biosensor 210, except for the reagent 1564. Reagent 364 is dispensed onto the electrode fingers 284 as discussed above with reference to biosensor 710 of FIG. 14.

Although the invention has been described in detail with reference to a preferred embodiment, variations and modifications exist within the scope and spirit of the invention, on as described and defined in the following claims.

What is claimed is:

1. A method of making a biosensor, the method comprising the steps of:
   providing an electrically conductive material on a base; and
   forming electrode patterns on the base using broad field laser ablation, wherein at least two electrode patterns have different feature sizes, wherein at least one electrode pattern has at least one edge extending between two points, a standard deviation of the edge from a line extending between two points is less than about 6 μm.

2. The method of claim 1 wherein the conductive material is selected from the group consisting of gold, platinum, palladium, iridium, and indium tin oxide.

3. The method of claim 1 wherein the base is a polymer.

4. The method of claim 1 wherein the forming step includes removing at least 2% of the conductive material from the base.

5. The method of claim 4 wherein at least 50% of the conductive material is removed from the base.

6. The method of claim 4 wherein at least 90% of the conductive material is removed from the base.

7. The method of claim 1 wherein the laser ablation is performed by a laser apparatus and at least one electrode pattern is formed with pulses of a laser beam from the laser apparatus.

8. The method of claim 1 wherein at least one electrode pattern is an interlacing pattern.

9. The method of claim 1 wherein the standard deviation is less than about 2 μm.

10. The method of claim 1 wherein the standard deviation is less than about 1.0 μm.

11. The method of claim 1 further comprising the step of placing a reagent on at least one of the electrode patterns.

12. The method of claim 1 wherein the laser ablation is performed by a laser apparatus and at least one electrode pattern is formed with a single pulse of a laser beam from the laser apparatus.

13. The method of claim 1 wherein the laser ablation is performed by a laser apparatus that produces a laser beam having a dimension that is greater than a feature size of at least one electrode pattern.

14. The method of claim 1 wherein at least one electrode pattern is formed by the forming step in less than about 0.25 seconds.

15. The method of claim 1 wherein at least one electrode pattern is formed by the forming step in less than about 50 nanoseconds.

16. The method of claim 1 wherein at least one electrode pattern is formed by the forming step in about 25 nanoseconds.

17. A method of making a biosensor, the method comprising the steps of:
   providing an electrically conductive material on a base; and
   forming electrode patterns on the base using broad field laser ablation, wherein at least two electrode patterns have different feature sizes, wherein the at least one electrode pattern has electrode fingers that cooperate with one another to define an electrode gap having a pre-determined width value, a standard deviation of the gap from the width value is less than about 4 μm.

18. The method of claim 17 wherein the gap standard deviation is less than about 3 μm.

19. The method of claim 17 wherein the gap standard devialion is less than about 1.0 μm.

20. A method of making a biosensor, the method comprising the steps of:
   providing an electrically conductive material on a base; and
   partially removing the conductive material using laser ablation from the base so that less than 90% of the conductive material remains on the base and at least one electrode pattern is formed from the conductive material, the at least one electrode pattern having an edge extending between two points, a standard deviation of the edge from a line extending between two points being less than about 6 µm.

21. The method of claim 20 wherein the standard deviation is less than about 2 µm.

22. The method of claim 20 wherein the standard deviation is less than about 1 µm.

23. The method of claim 20 wherein at least one electrode pattern is formed in less than about 0.25 seconds.

24. The method of claim 20 wherein at least one electrode pattern is formed in less than about 50 nanoseconds.

25. The method of claim 20 wherein said electrode pattern is formed in about 25 nanoseconds.

26. The method of claim 20 wherein the at least one electrode pattern has electrode fingers that cooperate with one another to define an electrode gap having a pre-determined width value, a standard deviation of the gap from the width value is less than about 4 µm.

27. The method of claim 26 wherein the gap standard deviation is less than about 3 µm.

28. The method ef claim 26 wherein the gap standard deviation is less than about 1.0 µm.

29. The method of claim 20 wherein less than 50% of the conductive material remains on the base.

30. The method of claim 20 wherein less than 10% of the conductive material remains on the base.

31. The method oF claim 20 wherein the conductive material is removed using laser ablation.

32. A method of making a biosensor, the method comprising the steps of: providing an electrically conductive material on a base,
forming electrode patterns on the base using broad field laser ablation, wherein at least two electrode patterns have different feature sizes, and
extending a cover over the base, the cover and base cooperating to define a sample-receiving chamber and at least a portion of the electrode patterns are positioned in the sample-receiving chamber.

33. The niethod of claim 32 wherein the conductive material is selected from the group consisting of gold, platinum, palladium, iridium, and indium tin oxide.

34. The method of claim 32 wherein the base is a polymer.

35. The method of claim 32 wherein the forming step includes removing at least 2% of the conductive material from the base.

36. The method of claim 35 wherein at least 90% of the conductive material is removed from the base.

37. The method of claim 32 wherein the laser ablation is performed by a laser apparatus and at least one electrode pattern is formed with pulses of a laser beam from the laser apparatus.

38. The method of claim 32 wherein at least one electrode pattern is an interlacing pattern.

39. The method of claim 32 wherein at least one electrode pattern has at least one edge extending between two points and a standard deviation of the edge from a line extending between two points is less than about 2 µm.

40. The method of claim 39 wherein the standard deviation is less than about 1.5 µm.

41. The method of claim 32 wherein the at least one electrode pattern has electrode fingers that cooperate with one another to define an electrode gap having a pre-determined width value, a standard deviation of the gap from the width value is less than about 2 µm.

42. The method of claim 41 wherein the standard deviation is less than about 1.75 µm.

43. The method of claim 32 further comprising the step of placing a reagent on at least one of the electrode patterns.

44. The method of claim 32 wherein the laser ablation is performed by a laser apparatus that produces a laser beam having a dimension that is greater than a feature size of at least one electrode pattern.

45. The method of claim 32 wherein at least one electrode pattern is formed in less than about 50 nanoseconds.

46. The method of claim 32 wherein said electrode pattern is formed in about 25 nanoseconds.

* * * * *